United States Patent [19]

Dasmahapatra et al.

[11] Patent Number: 5,843,752

[45] Date of Patent: Dec. 1, 1998

[54] SOLUBLE ACTIVE HEPATITIS C VIRUS PROTEASE

[75] Inventors: Bimalendu Dasmahapatra, Nutley; Nancy J. Butkiewicz, Plainfield, both of N.J.

[73] Assignee: Schering Corporation, Kenilworth, N.J.

[21] Appl. No.: 440,409

[22] Filed: May 12, 1995

[51] Int. Cl.$^6$ ...................................................... C12N 9/50
[52] U.S. Cl. ........................ 435/219; 435/69.7; 435/69.1; 435/320.1; 435/252.3; 435/172.3; 530/300; 536/23.2; 536/23.72
[58] Field of Search ................................ 435/69.1, 320.1, 435/252.3, 172.3, 219, 69.7; 530/300; 536/23.2, 23.72

[56] References Cited

U.S. PATENT DOCUMENTS

| | | | |
|---|---|---|---|
| 4,784,950 | 11/1988 | Hagen et al. | 435/68 |
| 5,371,017 | 12/1994 | Houghton et al. | 435/320.1 |
| 5,372,928 | 12/1994 | Miyamura et al. | 435/5 |
| 5,585,258 | 12/1996 | Houghton et al. | 435/219 |
| 5,597,691 | 1/1997 | Houghton et al. | 435/23 |
| 5,714,371 | 2/1998 | Ramanathan et al. | 435/219 |
| 5,739,002 | 4/1998 | De Francesco et al. | 435/23 |

OTHER PUBLICATIONS

Failla et al. J Virol (1994) 68:3753–3760 "Both NS3 and NS4A are Required for Proteolytic Processing of Hepatitis C Virus Nonstructural Proteins" Novagen Catalog (1991).
Bartenschlager et al. *J. Virology* 68: 5045–5055 (1994).
Bartenschlager et al. *J. Virology* 69: 198–205 (1995).
Failla et al. *J. Virology* 69: 1769–1777 (1995).
Lin et al., *J. Virology* 68: 8147–8157 (1994).
Pizza et al., *Proc. Natl. Acad. Sci U.S.A.* 91: 888–892 (1994).
Tanji et al., *J. Virology* 69: 1575–1581 (1995).

*Primary Examiner*—Robert A. Wax
*Assistant Examiner*—Enzique D. Longton
*Attorney, Agent, or Firm*—Jaye P. McLaughlin

[57] ABSTRACT

Soluble covalent HCV NS3–NS4A complexes comprising the catalytic domain of native HICV NS3 protease fused to an HCV NS4A cofactor, wherein the cofactor has been modified to prevent cleavage by the HCV NS3 protease.

5 Claims, 8 Drawing Sheets

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 549 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: HCV NS3 Protease ( x i ) SEQUENCE DESCRIPTION: SEQ ID NO: 1:

```
GCG   CCC   ATC   ACG   GCG   TAC   GCC   CAG   CAG   ACG   AGA   GGC   CTC   CTA   GGG            4 5
Ala   Pro   Ile   Thr   Ala   Tyr   Ala   Gln   Gln   Thr   Arg   Gly   Leu   Leu   Gly
 1                     5                              1 0                             1 5

TGT   ATA   ATC   ACC   AGC   CTG   ACT   GGC   CGG   GAC   AAA   AAC   CAA   GTG   GAG            9 0
Cys   Ile   Ile   Thr   Ser   Leu   Thr   Gly   Arg   Asp   Lys   Asn   Gln   Val   Glu
                       2 0                            2 5                             3 0

GGT   GAG   GTC   CAG   ATC   GTG   TCA   ACT   GCT   ACC   CAA   ACC   TTC   CTG   GCA          1 3 5
Gly   Glu   Val   Gln   Ile   Val   Ser   Thr   Ala   Thr   Gln   Thr   Phe   Leu   Ala
                              3 5                            4 0                           4 5

ACG   TGC   ATC   AAT   GGG   GTA   TGC   TGG   ACT   GTC   TAC   CAC   GGG   GCC   GGA          1 8 0
Thr   Cys   Ile   Asn   Gly   Val   Cys   Trp   Thr   Val   Tyr   His   Gly   Ala   Gly
                              5 0                            5 5                           6 0

ACG   AGG   ACC   ATC   GCA   TCA   CCC   AAG   GGT   CCT   GTC   ATC   CAG   ATG   TAT          2 2 5
Thr   Arg   Thr   Ile   Ala   Ser   Pro   Lys   Gly   Pro   Val   Ile   Gln   Met   Tyr
                              6 5                            7 0                           7 5

ACC   AAT   GTG   GAC   CAA   GAC   CTT   GTG   GGC   TGG   CCC   GCT   CCT   CAA   GGT          2 7 0
Thr   Asn   Val   Asp   Gln   Asp   Leu   Val   Gly   Trp   Pro   Ala   Pro   Gln   Gly
```

|     |     |     |     |     | 80  |     |     |     | 85  |     |     |     |     | 90  |     |     |
| --- | --- | --- | --- | --- | --- | --- | --- | --- | --- | --- | --- | --- | --- | --- | --- | --- |
| TCC | CGC | TCA | TTG | ACA | CCC | TGC | ACC | TGC | GGC | TCC | TCG | GAC | CTT | TAC |     | 315 |
| Ser | Arg | Ser | Leu | Thr | Pro | Cys | Thr | Cys | Gly | Ser | Ser | Asp | Leu | Tyr |     |     |
|     |     |     |     | 95  |     |     |     |     | 100 |     |     |     |     | 105 |     |     |
| CTG | GTT | ACG | AGG | CAC | GCC | GAC | GTC | ATT | CCC | GTG | CGC | CGG | CGA | GGT |     | 360 |
| Leu | Val | Thr | Arg | His | Ala | Asp | Val | Ile | Pro | Val | Arg | Arg | Arg | Gly |     |     |
|     |     |     |     | 110 |     |     |     |     | 115 |     |     |     |     | 120 |     |     |
| GAT | AGC | AGG | GGT | AGC | CTG | CTT | TCG | CCC | CGG | CCC | ATT | TCC | TAC | CTA |     | 405 |
| Asp | Ser | Arg | Gly | Ser | Leu | Leu | Ser | Pro | Arg | Pro | Ile | Ser | Tyr | Leu |     |     |
|     |     |     |     | 125 |     |     |     |     | 130 |     |     |     |     | 135 |     |     |
| AAA | GGC | TCC | TCG | GGG | GGT | CCG | CTG | TTG | TGC | CCC | GCG | GGA | CAC | GCC |     | 450 |
| Lys | Gly | Ser | Ser | Gly | Gly | Pro | Leu | Leu | Cys | Pro | Ala | Gly | His | Ala |     |     |
|     |     |     |     | 140 |     |     |     |     | 145 |     |     |     |     | 150 |     |     |
| GTG | GGC | CTA | TTC | AGG | GCC | GCG | GTG | TGC | ACC | CGT | GGA | GTG | ACC | AAG |     | 495 |
| Val | Gly | Leu | Phe | Arg | Ala | Ala | Val | Cys | Thr | Arg | Gly | Val | Thr | Lys |     |     |
|     |     |     |     | 155 |     |     |     |     | 160 |     |     |     |     | 165 |     |     |
| GCG | GTG | GAC | TTT | ATC | CCT | GTG | GAG | AAC | CTA | GAG | ACA | ACC | ATG | AGA |     | 540 |
| Ala | Val | Asp | Phe | Ile | Pro | Val | Glu | Asn | Leu | Glu | Thr | Thr | Met | Arg |     |     |
|     |     |     |     | 170 |     |     |     |     | 175 |     |     |     |     | 180 |     |     |
| TCC | CCG | GTG |     |     |     |     |     |     |     |     |     |     |     |     |     | 549 |
| Ser | Pro | Val |     |     |     |     |     |     |     |     |     |     |     |     |     |     |

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

| Arg | Lys | Lys | Lys | Arg | Arg |
| --- | --- | --- | --- | --- | --- |
|     |     |     |     | 5   |     |

( 2 ) INFORMATION FOR SEQ ID NO:3:

( i ) SEQUENCE CHARACTERISTICS:
        ( A ) LENGTH: 567 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:

( x i ) SEQUENCE DESCRIPTION: SEQ ID NO: 3:

| GCG | CCC | ATC | ACG | GCG | TAC | GCC | CAG | CAG | ACG | AGA | GGC | CTC | CTA | GGG |     | 45  |
| --- | --- | --- | --- | --- | --- | --- | --- | --- | --- | --- | --- | --- | --- | --- | --- | --- |
| Ala | Pro | Ile | Thr | Ala | Tyr | Ala | Gln | Gln | Thr | Arg | Gly | Leu | Leu | Gly |     |     |
| 1   |     |     |     | 5   |     |     |     |     | 10  |     |     |     |     | 15  |     |     |
| TGT | ATA | ATC | ACC | AGC | CTG | ACT | GGC | CGG | GAC | AAA | AAC | CAA | GTG | GAG |     | 90  |
| Cys | Ile | Ile | Thr | Ser | Leu | Thr | Gly | Arg | Asp | Lys | Asn | Gln | Val | Glu |     |     |
|     |     |     |     | 20  |     |     |     |     | 25  |     |     |     |     | 30  |     |     |
| GGT | GAG | GTC | CAG | ATC | GTG | TCA | ACT | GCT | ACC | CAA | ACC | TTC | CTG | GCA |     | 135 |
| Gly | Glu | Val | Gln | Ile | Val | Ser | Thr | Ala | Thr | Gln | Thr | Phe | Leu | Ala |     |     |
|     |     |     |     | 35  |     |     |     |     | 40  |     |     |     |     | 45  |     |     |
| ACG | TGC | ATC | AAT | GGG | GTA | TGC | TGG | ACT | GTC | TAC | CAC | GGG | GCC | GGA |     | 180 |
| Thr | Cys | Ile | Asn | Gly | Val | Cys | Trp | Thr | Val | Tyr | His | Gly | Ala | Gly |     |     |
|     |     |     |     | 50  |     |     |     |     | 55  |     |     |     |     | 60  |     |     |
| ACG | AGG | ACC | ATC | GCA | TCA | CCC | AAG | GGT | CCT | GTC | ATC | CAG | ATG | TAT |     | 225 |
| Thr | Arg | Thr | Ile | Ala | Ser | Pro | Lys | Gly | Pro | Val | Ile | Gln | Met | Tyr |     |     |
|     |     |     |     | 65  |     |     |     |     | 70  |     |     |     |     | 75  |     |     |

| | | | | | | | | | | | | | | | |
|---|---|---|---|---|---|---|---|---|---|---|---|---|---|---|---|
|ACC|AAT|GTG|GAC|CAA|GAC|CTT|GTG|GGC|TGG|CCC|GCT|CCT|CAA|GGT|270|
|Thr|Asn|Val|Asp|Gln|Asp|Leu|Val|Gly|Trp|Pro|Ala|Pro|Gln|Gly||
| | | |80| | | |85| | | | | |90| |

|TCC|CGC|TCA|TTG|ACA|CCC|TGC|ACC|TGC|GGC|TCC|TCG|GAC|CTT|TAC|315|
|---|---|---|---|---|---|---|---|---|---|---|---|---|---|---|---|
|Ser|Arg|Ser|Leu|Thr|Pro|Cys|Thr|Cys|Gly|Ser|Ser|Asp|Leu|Tyr||
| | | | |95| | | |100| | | | |105| |

|CTG|GTT|ACG|AGG|CAC|GCC|GAC|GTC|ATT|CCC|GTG|CGC|GGG|CGA|GGT|360|
|---|---|---|---|---|---|---|---|---|---|---|---|---|---|---|---|
|Leu|Val|Thr|Arg|His|Ala|Asp|Val|Ile|Pro|Val|Arg|Arg|Arg|Gly||
| | | |110| | | |115| | | | |120| | |

|GAT|AGC|AGG|GGT|AGC|CTG|CTT|TCG|CCC|CGG|CCC|ATT|TCC|TAC|CTA|405|
|---|---|---|---|---|---|---|---|---|---|---|---|---|---|---|---|
|Asp|Ser|Arg|Gly|Ser|Leu|Leu|Ser|Pro|Arg|Pro|Ile|Ser|Tyr|Leu||
| | | | |125| | | |130| | | | |135| |

|AAA|GGC|TCC|TCG|GGG|GGT|CCG|CTG|TTG|TGC|CCC|GCG|GGA|CAC|GCC|450|
|---|---|---|---|---|---|---|---|---|---|---|---|---|---|---|---|
|Lys|Gly|Ser|Ser|Gly|Gly|Pro|Leu|Leu|Cys|Pro|Ala|Gly|His|Ala||
| | | | |140| | | |145| | | | |150| |

|GTG|GGC|CTA|TTC|AGG|GCC|GCG|GTG|TGC|ACC|CGT|GGA|GTG|ACC|AAG|495|
|---|---|---|---|---|---|---|---|---|---|---|---|---|---|---|---|
|Val|Gly|Leu|Phe|Arg|Ala|Ala|Val|Cys|Thr|Arg|Gly|Val|Thr|Lys||
| | | | |155| | | |160| | | | |165| |

|GCG|GTG|GAC|TTT|ATC|CCT|GTG|GAG|AAC|CTA|GAG|ACA|ACC|ATG|AGA|540|
|---|---|---|---|---|---|---|---|---|---|---|---|---|---|---|---|
|Ala|Val|Asp|Phe|Ile|Pro|Val|Glu|Asn|Leu|Glu|Thr|Thr|Met|Arg||
| | | | |170| | | |175| | | | |180| |

|TCC|CCG|GTG|AGA|AAG|AAG|AAG|AGA|AGA| | | | | | |567|
|---|---|---|---|---|---|---|---|---|---|---|---|---|---|---|---|
|Ser|Pro|Val|Arg|Lys|Lys|Lys|Arg|Arg| | | | | | | |
| | | | |185| | | | | | | | | | | |

( 2 ) INFORMATION FOR SEQ ID NO:4:

( i ) SEQUENCE CHARACTERISTICS:
        ( A ) LENGTH: 603 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: pBJ1022(His/NS3 (182)/H.T.

( x i ) SEQUENCE DESCRIPTION: SEQ ID NO: 4:

|ATG|AGA|GGA|TCG|CAT|CAC|CAT|CAC|CAT|CAC|ACG|GAT|CCG|CCC|ATC|45|
|---|---|---|---|---|---|---|---|---|---|---|---|---|---|---|---|
|Met|Arg|Gly|Ser|His|His|His|His|His|His|Thr|Asp|Pro|Pro|Ile||
|1| | | |5| | | | |10| | | | |15| |

|ACG|GCG|TAC|GCC|CAG|CAG|ACG|AGA|GGC|CTC|CTA|GGG|TGT|ATA|ATC|90|
|---|---|---|---|---|---|---|---|---|---|---|---|---|---|---|---|
|Thr|Ala|Tyr|Ala|Gln|Gln|Thr|Arg|Gly|Leu|Leu|Gly|Cys|Ile|Ile||
| | | | |20| | | |25| | | | |30| |

|ACC|AGC|CTG|ACT|GGC|CGG|GAC|AAA|AAC|CAA|GTG|GAG|GGT|GAG|GTC|135|
|---|---|---|---|---|---|---|---|---|---|---|---|---|---|---|---|
|Thr|Ser|Leu|Thr|Gly|Arg|Asp|Lys|Asn|Gln|Val|Glu|Gly|Glu|Val||
| | | | |35| | | |40| | | | |45| |

|CAG|ATC|GTG|TCA|ACT|GCT|ACC|CAA|ACC|TTC|CTG|GCA|ACG|TGC|ATC|180|
|---|---|---|---|---|---|---|---|---|---|---|---|---|---|---|---|
|Gln|Ile|Val|Ser|Thr|Ala|Thr|Gln|Thr|Phe|Leu|Ala|Thr|Cys|Ile||
| | | | |50| | | |55| | | | |60| |

|AAT|GGG|GTA|TGC|TGG|ACT|GTC|TAC|CAC|GGG|GCC|GGA|ACG|AGG|ACC|225|
|---|---|---|---|---|---|---|---|---|---|---|---|---|---|---|---|
|Asn|Gly|Val|Cys|Trp|Thr|Val|Tyr|His|Gly|Ala|Gly|Thr|Arg|Thr||
| | | | |65| | | |70| | | | |75| |

|ATC|GCA|TCA|CCC|AAG|GGT|CCT|GTC|ATC|CAG|ATG|TAT|ACC|AAT|GTG|270|
|---|---|---|---|---|---|---|---|---|---|---|---|---|---|---|---|
|Ile|Ala|Ser|Pro|Lys|Gly|Pro|Val|Ile|Gln|Met|Tyr|Thr|Asn|Val||
| | | | |80| | | |85| | | | |90| |

|GAC|CAA|GAC|CTT|GTG|GGC|TGG|CCC|GCT|CCT|CAA|GGT|TCC|CGC|TCA|315|
|---|---|---|---|---|---|---|---|---|---|---|---|---|---|---|---|
|Asp|Gln|Asp|Leu|Val|Gly|Trp|Pro|Ala|Pro|Gln|Gly|Ser|Arg|Ser||
| | | | |95| | | |100| | | | |105| |

|TTG|ACA|CCC|TGC|ACC|TGC|GGC|TCC|TCG|GAC|CTT|TAC|CTG|GTT|ACG|360|
|---|---|---|---|---|---|---|---|---|---|---|---|---|---|---|---|
|Leu|Thr|Pro|Cys|Thr|Cys|Gly|Ser|Ser|Asp|Leu|Tyr|Leu|Val|Thr||
| | | | |110| | | |115| | | | |120| |

```
AGG  CAC  GCC  GAC  GTC  ATT  CCC  GTG  CGC  CGG  CGA  GGT  GAT  AGC  AGG        405
Arg  His  Ala  Asp  Val  Ile  Pro  Val  Arg  Arg  Arg  Gly  Asp  Ser  Arg
               125                      130                      135

GGT  AGC  CTG  CTT  TCG  CCC  CGG  CCC  ATT  TCC  TAC  CTA  AAA  GGC  TCC        450
Gly  Ser  Leu  Leu  Ser  Pro  Arg  Pro  Ile  Ser  Tyr  Leu  Lys  Gly  Ser
               140                      145                      150

TCG  GGG  GGT  CCG  CTG  TTG  TGC  CCC  GCG  GGA  CAC  GCC  GTG  GGC  CTA        495
Ser  Gly  Gly  Pro  Leu  Leu  Cys  Pro  Ala  Gly  His  Ala  Val  Gly  Leu
               155                      160                      165

TTC  AGG  GCC  GCG  GTG  TGC  ACC  CGT  GGA  GTG  ACC  AAG  GCG  GTG  GAC        540
Phe  Arg  Ala  Ala  Val  Cys  Thr  Arg  Gly  Val  Thr  Lys  Ala  Val  Asp
               170                      175                      180

TTT  ATC  CCT  GTG  GAG  AAC  CTA  GAG  ACA  ACC  ATG  AGA  TCC  CCG  GTG        585
Phe  Ile  Pro  Val  Glu  Asn  Leu  Glu  Thr  Thr  Met  Arg  Ser  Pro  Val
               185                      190                      195

AGA  AAG  AAG  AAG  AGA  AGA                                                      603
Arg  Lys  Lys  Lys  Arg  Arg
               200
```

( 2 ) INFORMATION FOR SEQ ID NO:5:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: pT5His/HIV/183 No solubilizing motif ( x i ) SEQUENCE DESCRIPTION: SEQ ID NO: 5:

```
ATG  AGA  GGA  TCG  CAT  CAC  CAT  CAC  CAT  CAC  GGA  TCC  CAT  AAG  GCA         45
Met  Arg  Gly  Ser  His  His  His  His  His  His  Gly  Ser  His  Lys  Ala
1                   5                        10                      15

AGA  GTT  TTG  GCT  GAA  GCA  ATG  AGC  CAT  GGT  ACC  ATG  GCG  CCC  ATC         90
Arg  Val  Leu  Ala  Glu  Ala  Met  Ser  His  Gly  Thr  Met  Ala  Pro  Ile
                    20                       25                      30

ACG  GCG  TAC  GCC  CAG  CAG  ACG  AGA  GGC  CTC  CTA  GGG  TGT  ATA  ATC        135
Thr  Ala  Tyr  Ala  Gln  Gln  Thr  Arg  Gly  Leu  Leu  Gly  Cys  Ile  Ile
                    35                       40                      45

ACC  AGC  CTG  ACT  GGC  CGG  GAC  AAA  AAC  CAA  GTG  GAG  GGT  GAG  GTC        180
Thr  Ser  Leu  Thr  Gly  Arg  Asp  Lys  Asn  Gln  Val  Glu  Gly  Glu  Val
                    50                       55                      60

CAG  ATC  GTG  TCA  ACT  GCT  ACC  CAA  ACC  TTC  CTG  GCA  ACG  TGC  ATC        225
Gln  Ile  Val  Ser  Thr  Ala  Thr  Gln  Thr  Phe  Leu  Ala  Thr  Cys  Ile
                    65                       70                      75

AAT  GGG  GTA  TGC  TGG  ACT  GTC  TAC  CAC  GGG  GCC  GGA  ACG  AGG  ACC        270
Asn  Gly  Val  Cys  Trp  Thr  Val  Tyr  His  Gly  Ala  Gly  Thr  Arg  Thr
                    80                       85                      90

ATC  GCA  TCA  CCC  AAG  GGT  CCT  GTC  ATC  CAG  ATG  TAT  ACC  AAT  GTG        315
Ile  Ala  Ser  Pro  Lys  Gly  Pro  Val  Ile  Gln  Met  Tyr  Thr  Asn  Val
                    95                      100                     105

GAC  CAA  GAC  CTT  GTG  GGC  TGG  CCC  GCT  CCT  CAA  GGT  TCC  CGC  TCA        360
Asp  Gln  Asp  Leu  Val  Gly  Trp  Pro  Ala  Pro  Gln  Gly  Ser  Arg  Ser
                   110                      115                     120

TTG  ACA  CCC  TGC  ACC  TGC  GGC  TCC  TCG  GAC  CTT  TAC  CTG  GTT  ACG        405
Leu  Thr  Pro  Cys  Thr  Cys  Gly  Ser  Ser  Asp  Leu  Tyr  Leu  Val  Thr
                   125                      130                     135

AGG  CAC  GCC  GAC  GTC  ATT  CCC  GTG  CGC  CGG  CGA  GGT  GAT  AGC  AGG        450
Arg  His  Ala  Asp  Val  Ile  Pro  Val  Arg  Arg  Arg  Gly  Asp  Ser  Arg
                   140                      145                     150
```

```
GGT  AGC  CTG  CTT  TCG  CCC  CGG  CCC  ATT  TCC  TAC  CTA  AAA  GGC  TCC       495
Gly  Ser  Leu  Leu  Ser  Pro  Arg  Pro  Ile  Ser  Tyr  Leu  Lys  Gly  Ser
               155                      160                     165

TCG  GGG  GGT  CCG  CTG  TTG  TGC  CCC  GCG  GGA  CAC  GCC  GTG  GGC  CTA       540
Ser  Gly  Gly  Pro  Leu  Leu  Cys  Pro  Ala  Gly  His  Ala  Val  Gly  Leu
               170                      175                     180

TTC  AGG  GCC  GCG  GTG  TGC  ACC  CGT  GGA  GTG  ACC  AAG  GCG  GTG  GAC       585
Phe  Arg  Ala  Ala  Val  Cys  Thr  Arg  Gly  Val  Thr  Lys  Ala  Val  Asp
               185                      190                     195

TTT  ATC  CCT  GTG  GAG  AAC  CTA  GAG  ACA  ACC  ATG  AGA  TCC  CCG  GTG       630
Phe  Ile  Pro  Val  Glu  Asn  Leu  Glu  Thr  Thr  Met  Arg  Ser  Pro  Val
               200                      205                     210
```

(2) INFORMATION FOR SEQ ID NO:6:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: NS4A (xi) SEQUENCE DESCRIPTION: SEQ ID NO: 6:

```
AGC  ACC  TGG  GTG  CTC  GTT  GGC  GGC  GTC  CTG  GCT  GCT  CTG  GCC  GCG        45
Ser  Thr  Trp  Val  Leu  Val  Gly  Gly  Val  Leu  Ala  Ala  Leu  Ala  Ala
1                        5                       10                      15

TAT  TGC  CTG  TCA  ACA  GGC  TGC  GTG  GTC  ATA  GTG  GGC  AGG  ATT  GTC        90
Tyr  Cys  Leu  Ser  Thr  Gly  Cys  Val  Val  Ile  Val  Gly  Arg  Ile  Val
               20                       25                      30

TTG  TCC  GGG  AAG  CCG  GCA  ATT  ATA  CCT  GAC  AGG  GAG  GTT  CTC  TAC       135
Leu  Ser  Gly  Lys  Pro  Ala  Ile  Ile  Pro  Asp  Arg  Glu  Val  Leu  Tyr
               35                       40                      45

CAG  GAG  TTC  GAT  GAG  ATG  GAA  GAG  TGC                                     162
Gln  Glu  Phe  Asp  Glu  Met  Glu  Glu  Cys
               50
```

(2) INFORMATION FOR SEQ ID NO:7:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: NS3 +NS4A (xi) SEQUENCE DESCRIPTION: SEQ ID NO: 7:

```
GCG  CCC  ATC  ACG  GCG  TAC  GCC  CAG  CAG  ACG  AGA  GGC  CTC  CTA  GGG        45
Ala  Pro  Ile  Thr  Ala  Tyr  Ala  Gln  Gln  Thr  Arg  Gly  Leu  Leu  Gly
1                        5                       10                      15

TGT  ATA  ATC  ACC  AGC  CTG  ACT  GGC  CGG  GAC  AAA  AAC  CAA  GTG  GAG        90
Cys  Ile  Ile  Thr  Ser  Leu  Thr  Gly  Arg  Asp  Lys  Asn  Gln  Val  Glu
               20                       25                      30

GGT  GAG  GTC  CAG  ATC  GTG  TCA  ACT  GCT  ACC  CAA  ACC  TTC  CTG  GCA       135
Gly  Glu  Val  Gln  Ile  Val  Ser  Thr  Ala  Thr  Gln  Thr  Phe  Leu  Ala
               35                       40                      45

ACG  TGC  ATC  AAT  GGG  GTA  TGC  TGG  ACT  GTC  TAC  CAC  GGG  GCC  GGA       180
Thr  Cys  Ile  Asn  Gly  Val  Cys  Trp  Thr  Val  Tyr  His  Gly  Ala  Gly
               50                       55                      60
```

```
ACG AGG ACC ATC GCA TCA CCC AAG GGT CCT GTC ATC CAG ATG TAT    225
Thr Arg Thr Ile Ala Ser Pro Lys Gly Pro Val Ile Gln Met Tyr
            65                  70                  75

ACC AAT GTG GAC CAA GAC CTT GTG GGC TGG CCC GCT CCT CAA GGT    270
Thr Asn Val Asp Gln Asp Leu Val Gly Trp Pro Ala Pro Gln Gly
            80                  85                  90

TCC CGC TCA TTG ACA CCC TGC ACC TGC GGC TCC TCG GAC CTT TAC    315
Ser Arg Ser Leu Thr Pro Cys Thr Cys Gly Ser Ser Asp Leu Tyr
            95                  100                 105

CTG GTT ACG AGG CAC GCC GAC GTC ATT CCC GTG CGC GGG CGA GGT    360
Leu Val Thr Arg His Ala Asp Val Ile Pro Val Arg Arg Arg Gly
            110                 115                 120

GAT AGC AGG GGT AGC CTG CTT TCG CCC CGG CCC ATT TCC TAC CTA    405
Asp Ser Arg Gly Ser Leu Leu Ser Pro Arg Pro Ile Ser Tyr Leu
            125                 130                 135

AAA GGC TCC TCG GGG GGT CCG CTG TTG TGC CCC GCG GGA CAC GCC    450
Lys Gly Ser Ser Gly Gly Pro Leu Leu Cys Pro Ala Gly His Ala
            140                 145                 150

GTG GGC CTA TTC AGG GCC GCG GTG TGC ACC CGT GGA GTG ACC AAG    495
Val Gly Leu Phe Arg Ala Ala Val Cys Thr Arg Gly Val Thr Lys
            155                 160                 165

GCG GTG GAC TTT ATC CCT GTG GAG AAC CTA GAG ACA ACC ATG AGA    540
Ala Val Asp Phe Ile Pro Val Glu Asn Leu Glu Thr Thr Met Arg
            170                 175                 180

TCC CCG GGG GTG CTC GTT GGC GGC GTC CTG GCT GCT CTG GCC GCG    585
Ser Pro Gly Val Leu Val Gly Gly Val Leu Ala Ala Leu Ala Ala
            185                 190                 195

TAT TGC CTG TCA ACA GGC TGC GTG GTC ATA GTG GGC AGG ATT GTC    630
Tyr Cys Leu Ser Thr Gly Cys Val Val Ile Val Gly Arg Ile Val
            200                 205                 210

TTG TCC GGG AAG CCG GCA ATT ATA CCT GAC AGG GAG GTT CTC TAC    675
Leu Ser Gly Lys Pro Ala Ile Ile Pro Asp Arg Glu Val Leu Tyr
            215                 220                 225

CAG GAG TTC GAT GAG ATG GAA GAG TGC                            702
Gln Glu Phe Asp Glu Met Glu Glu Cys
            230
```

(2) INFORMATION FOR SEQ ID NO:8:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: pNB182[0081]4AHT (xi) SEQUENCE DESCRIPTION: SEQ ID NO: 8:

```
ATG AGA GGA TCG CAT CAC CAT CAC CAT CAC GGA TCC CAT AAG GCA    45
Met Arg Gly Ser His His His His His His Gly Ser His Lys Ala
1               5                   10                  15

AGA GTT TTG GCT GAA GCA ATG AGC CAT GGT ACC ATG GCG CCC ATC    90
Arg Val Leu Ala Glu Ala Met Ser His Gly Thr Met Ala Pro Ile
            20                  25                  30

ACG GCG TAC GCC CAG CAG ACG AGA GGC CTC CTA GGG TGT ATA ATC    135
Thr Ala Tyr Ala Gln Gln Thr Arg Gly Leu Leu Gly Cys Ile Ile
            35                  40                  45

ACC AGC CTG ACT GGC CGG GAC AAA AAC CAA GTG GAG GGT GAG GTC    180
Thr Ser Leu Thr Gly Arg Asp Lys Asn Gln Val Glu Gly Glu Val
            50                  55                  60
```

| | | | | | | | | | | | | | | | |
|---|---|---|---|---|---|---|---|---|---|---|---|---|---|---|---|
| CAG | ATC | GTG | TCA | ACT | GCT | ACC | CAA | ACC | TTC | CTG | GCA | ACG | TGC | ATC | 225 |
| Gln | Ile | Val | Ser | Thr 65 | Ala | Thr | Gln | Thr 70 | Phe | Leu | Ala | Thr | Cys | Ile 75 | |
| AAT | GGG | GTA | TGC | TGG | ACT | GTC | TAC | CAC | GGG | GCC | GGA | ACG | AGG | ACC | 270 |
| Asn | Gly | Val | Cys | Trp 80 | Thr | Val | Tyr | His 85 | Gly | Ala | Gly | Thr | Arg | Thr 90 | |
| ATC | GCA | TCA | CCC | AAG | GGT | CCT | GTC | ATC | CAG | ATG | TAT | ACC | AAT | GTG | 315 |
| Ile | Ala | Ser | Pro | Lys 95 | Gly | Pro | Val | Ile 100 | Gln | Met | Tyr | Thr | Asn | Val 105 | |
| GAC | CAA | GAC | CTT | GTG | GGC | TGG | CCC | GCT | CCT | CAA | GGT | TCC | CGC | TCA | 360 |
| Asp | Gln | Asp | Leu | Val 110 | Gly | Trp | Pro | Ala 115 | Pro | Gln | Gly | Ser | Arg | Ser 120 | |
| TTG | ACA | CCC | TGC | ACC | TGC | GGC | TCC | TCG | GAC | CTT | TAC | CTG | GTT | ACG | 405 |
| Leu | Thr | Pro | Cys | Thr 125 | Cys | Gly | Ser | Ser 130 | Asp | Leu | Tyr | Leu | Val | Thr 135 | |
| AGG | CAC | GCC | GAC | GTC | ATT | CCC | GTG | CGC | CGG | CGA | GGT | GAT | AGC | AGG | 450 |
| Arg | His | Ala | Asp | Val 140 | Ile | Pro | Val | Arg 145 | Arg | Arg | Gly | Asp | Ser | Arg 150 | |
| GGT | AGC | CTG | CTT | TCG | CCC | CGG | CCC | ATT | TCC | TAC | CTA | AAA | GGC | TCC | 495 |
| Gly | Ser | Leu | Leu | Ser 155 | Pro | Arg | Pro | Ile 160 | Ser | Tyr | Leu | Lys | Gly | Ser 165 | |
| TCG | GGG | GGT | CCG | CTG | TTG | TGC | CCC | GCG | GGA | CAC | GCC | GTG | GGC | CTA | 540 |
| Ser | Gly | Gly | Pro | Leu 170 | Leu | Cys | Pro | Ala 175 | Gly | His | Ala | Val | Gly | Leu 180 | |
| TTC | AGG | GCC | GCG | GTG | TGC | ACC | CGT | GGA | GTG | ACC | AAG | GCG | GTG | GAC | 585 |
| Phe | Arg | Ala | Ala | Val 185 | Cys | Thr | Arg | Gly 190 | Val | Thr | Lys | Ala | Val | Asp 195 | |
| TTT | ATC | CCT | GTG | GAG | AAC | CTA | GAG | ACA | ACC | ATG | AGA | TCC | CCG | GGG | 630 |
| Phe | Ile | Pro | Val | Glu 200 | Asn | Leu | Glu | Thr 205 | Thr | Met | Arg | Ser | Pro | Gly 210 | |
| GTG | CTC | GTT | GGC | GGC | GTC | CTG | GCT | GCT | CTG | GCC | GCG | TAT | TGC | CTG | 675 |
| Val | Leu | Val | Gly | Gly 215 | Val | Leu | Ala | Ala 220 | Leu | Ala | Ala | Tyr | Cys | Leu 225 | |
| TCA | ACA | GGC | TGC | GTG | GTC | ATA | GTG | GGC | AGG | ATT | GTC | TTG | TCC | GGG | 720 |
| Ser | Thr | Gly | Cys | Val 230 | Val | Ile | Val | Gly 235 | Arg | Ile | Val | Leu | Ser | Gly 240 | |
| AAG | CCG | GCA | ATT | ATA | CCT | GAC | AGG | GAG | GTT | CTC | TAC | CAG | GAG | TTC | 765 |
| Lys | Pro | Ala | Ile | Ile 245 | Pro | Asp | Arg | Glu 250 | Val | Leu | Tyr | Gln | Glu | Phe 255 | |
| GAT | GAG | ATG | GAA | GAG | TGC | CGG | AAG | AAA | AAG | AGA | CGC | AAG | CTT | AAT | 810 |
| Asp | Glu | Met | Glu | Glu 260 | Cys | Arg | Lys | Lys 265 | Lys | Arg | Arg | Lys | Leu | Asn 270 | |

( 2 ) INFORMATION FOR SEQ ID NO:9:

( i ) SEQUENCE CHARACTERISTICS:
        ( A ) LENGTH: 711 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:

( x i ) SEQUENCE DESCRIPTION: SEQ ID NO: 9:

| | | | | | | | | | | | | | | | |
|---|---|---|---|---|---|---|---|---|---|---|---|---|---|---|---|
| GCG | CCC | ATC | ACG | GCG | TAC | GCC | CAG | CAG | ACG | AGA | GGC | CTC | CTA | GGG | 45 |
| Ala 1 | Pro | Ile | Thr | Ala 5 | Tyr | Ala | Gln | Gln 10 | Thr | Arg | Gly | Leu | Leu | Gly 15 | |
| TGT | ATA | ATC | ACC | AGC | CTG | ACT | GGC | CGG | GAC | AAA | AAC | CAA | GTG | GAG | 90 |
| Cys | Ile | Ile | Thr | Ser 20 | Leu | Thr | Gly | Arg 25 | Asp | Lys | Asn | Gln | Val | Glu 30 | |

| | | | | | | | | | | | | | | | |
|---|---|---|---|---|---|---|---|---|---|---|---|---|---|---|---|
|GGT|GAG|GTC|CAG|ATC|GTG|TCA|ACT|GCT|ACC|CAA|ACC|TTC|CTG|GCA|135|
|Gly|Glu|Val|Gln|Ile|Val|Ser|Thr|Ala|Thr|Gln|Thr|Phe|Leu|Ala| |
| | | | |35| | | |40| | | | | |45| |
|ACG|TGC|ATC|AAT|GGG|GTA|TGC|TGG|ACT|GTC|TAC|CAC|GGG|GCC|GGA|180|
|Thr|Cys|Ile|Asn|Gly|Val|Cys|Trp|Thr|Val|Tyr|His|Gly|Ala|Gly| |
| | | | |50| | | |55| | | | | |60| |
|ACG|AGG|ACC|ATC|GCA|TCA|CCC|AAG|GGT|CCT|GTC|ATC|CAG|ATG|TAT|225|
|Thr|Arg|Thr|Ile|Ala|Ser|Pro|Lys|Gly|Pro|Val|Ile|Gln|Met|Tyr| |
| | | | |65| | | |70| | | | | |75| |
|ACC|AAT|GTG|GAC|CAA|GAC|CTT|GTG|GGC|TGG|CCC|GCT|CCT|CAA|GGT|270|
|Thr|Asn|Val|Asp|Gln|Asp|Leu|Val|Gly|Trp|Pro|Ala|Pro|Gln|Gly| |
| | | | |80| | | |85| | | | | |90| |
|TCC|CGC|TCA|TTG|ACA|CCC|TGC|ACC|TGC|GGC|TCC|TCG|GAC|CTT|TAC|315|
|Ser|Arg|Ser|Leu|Thr|Pro|Cys|Thr|Cys|Gly|Ser|Ser|Asp|Leu|Tyr| |
| | | | |95| | | |100| | | | | |105| |
|CTG|GTT|ACG|AGG|CAC|GCC|GAC|GTC|ATT|CCC|GTG|CGC|GGG|CGA|GGT|360|
|Leu|Val|Thr|Arg|His|Ala|Asp|Val|Ile|Pro|Val|Arg|Arg|Arg|Gly| |
| | | | |110| | | |115| | | | | |120| |
|GAT|AGC|AGG|GGT|AGC|CTG|CTT|TCG|CCC|CGG|CCC|ATT|TCC|TAC|CTA|405|
|Asp|Ser|Arg|Gly|Ser|Leu|Leu|Ser|Pro|Arg|Pro|Ile|Ser|Tyr|Leu| |
| | | | |125| | | |130| | | | | |135| |
|AAA|GGC|TCC|TCG|GGG|GGT|CCG|CTG|TTG|TGC|CCC|GCG|GGA|CAC|GCC|450|
|Lys|Gly|Ser|Ser|Gly|Gly|Pro|Leu|Leu|Cys|Pro|Ala|Gly|His|Ala| |
| | | | |140| | | |145| | | | | |150| |
|GTG|GGC|CTA|TTC|AGG|GCC|GCG|GTG|TGC|ACC|CGT|GGA|GTG|ACC|AAG|495|
|Val|Gly|Leu|Phe|Arg|Ala|Ala|Val|Cys|Thr|Arg|Gly|Val|Thr|Lys| |
| | | | |155| | | |160| | | | | |165| |
|GCG|GTG|GAC|TTT|ATC|CCT|GTG|GAG|AAC|CTA|GAG|ACA|ACC|ATG|AGA|540|
|Ala|Val|Asp|Phe|Ile|Pro|Val|Glu|Asn|Leu|Glu|Thr|Thr|Met|Arg| |
| | | | |170| | | |175| | | | | |180| |
|TCC|CCG|GGG|GTG|CTC|GTT|GGC|GGC|GTC|CTG|GCT|GCT|CTG|GCC|GCG|585|
|Ser|Pro|Gly|Val|Leu|Val|Gly|Gly|Val|Leu|Ala|Ala|Leu|Ala|Ala| |
| | | | |185| | | |190| | | | | |195| |
|TAT|TGC|CTG|TCA|ACA|GGC|TGC|GTG|GTC|ATA|GTG|GGC|AGG|ATT|GTC|630|
|Tyr|Cys|Leu|Ser|Thr|Gly|Cys|Val|Val|Ile|Val|Gly|Arg|Ile|Val| |
| | | | |200| | | |205| | | | | |210| |
|TTG|TCC|GGG|AAG|CCG|GCA|ATT|ATA|CCT|GAC|AGG|GAG|GTT|CTC|TAC|675|
|Leu|Ser|Gly|Lys|Pro|Ala|Ile|Ile|Pro|Asp|Arg|Glu|Val|Leu|Tyr| |
| | | | |215| | | |220| | | | | |225| |
|CAG|GAG|TTC|GAT|GAG|ATG|GAA|GAG|AAG|GAG|ACA|GAG| | | |711|
|Gln|Glu|Phe|Asp|Glu|Met|Glu|Glu|Lys|Glu|Thr|Glu| | | | |
| | | | |230| | | |235| | | | | | | |

( 2 ) INFORMATION FOR SEQ ID NO:10:

( i ) SEQUENCE CHARACTERISTICS:
        ( A ) LENGTH: 750 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:

( x i ) SEQUENCE DESCRIPTION: SEQ ID NO: 10:

| | | | | | | | | | | | | | | | |
|---|---|---|---|---|---|---|---|---|---|---|---|---|---|---|---|
|ATG|AGA|GGA|TCG|CAT|CAC|CAT|CAC|CAT|CAC|ACG|GAT|CCG|GCG|CCC|45|
|Met|Arg|Gly|Ser|His|His|His|His|His|His|Thr|Asp|Pro|Ala|Pro| |
|1| | | |5| | | |10| | | | | |15| |
|ATC|ACG|GCG|TAC|GCC|CAG|CAG|ACG|AGA|GGC|CTC|CTA|GGG|TGT|ATA|90|
|Ile|Thr|Ala|Tyr|Ala|Gln|Gln|Thr|Arg|Gly|Leu|Leu|Gly|Cys|Ile| |
| | | | |20| | | |25| | | | | |30| |

```
ATC ACC AGC CTG ACT GGC CGG GAC AAA AAC CAA GTG GAG GGT GAG      135
Ile Thr Ser Leu Thr Gly Arg Asp Lys Asn Gln Val Glu Gly Glu
            35                  40                  45

GTC CAG ATC GTG TCA ACT GCT ACC CAA ACC TTC CTG GCA ACG TGC      180
Val Gln Ile Val Ser Thr Ala Thr Gln Thr Phe Leu Ala Thr Cys
            50                  55                  60

ATC AAT GGG GTA TGC TGG ACT GTC TAC CAC GGG GCC GGA ACG AGG      225
Ile Asn Gly Val Cys Trp Thr Val Tyr His Gly Ala Gly Thr Arg
            65                  70                  75

ACC ATC GCA TCA CCC AAG GGT CCT GTC ATC CAG ATG TAT ACC AAT      270
Thr Ile Ala Ser Pro Lys Gly Pro Val Ile Gln Met Tyr Thr Asn
            80                  85                  90

GTG GAC CAA GAC CTT GTG GGC TGG CCC GCT CCT CAA GGT TCC CGC      315
Val Asp Gln Asp Leu Val Gly Trp Pro Ala Pro Gln Gly Ser Arg
            95                  100                 105

TCA TTG ACA CCC TGC ACC TGC GGC TCC TCG GAC CTT TAC CTG GTT      360
Ser Leu Thr Pro Cys Thr Cys Gly Ser Ser Asp Leu Tyr Leu Val
            110                 115                 120

ACG AGG CAC GCC GAC GTC ATT CCC GTG CGC CGG CGA GGT GAT AGC      405
Thr Arg His Ala Asp Val Ile Pro Val Arg Arg Arg Gly Asp Ser
            125                 130                 135

AGG GGT AGC CTG CTT TCG CCC CGG CCC ATT TCC TAC CTA AAA GGC      450
Arg Gly Ser Leu Leu Ser Pro Arg Pro Ile Ser Tyr Leu Lys Gly
            140                 145                 150

TCC TCG GGG GGT CCG CTG TTG TGC CCC GCG GGA CAC GCC GTG GGC      495
Ser Ser Gly Gly Pro Leu Leu Cys Pro Ala Gly His Ala Val Gly
            155                 160                 165

CTA TTC AGG GCC GCG GTG TGC ACC CGT GGA GTG ACC AAG GCG GTG      540
Leu Phe Arg Ala Ala Val Cys Thr Arg Gly Val Thr Lys Ala Val
            170                 175                 180

GAC TTT ATC CCT GTG GAG AAC CTA GAG ACA ACC ATG AGA TCC CCG      585
Asp Phe Ile Pro Val Glu Asn Leu Glu Thr Thr Met Arg Ser Pro
            185                 190                 195

GGG GTG CTC GTT GGC GGC GTC CTG GCT GCT CTG GCC GCG TAT TGC      630
Gly Val Leu Val Gly Gly Val Leu Ala Ala Leu Ala Ala Tyr Cys
            200                 205                 210

CTG TCA ACA GGC TGC GTG GTC ATA GTG GGC AGG ATT GTC TTG TCC      675
Leu Ser Thr Gly Cys Val Val Ile Val Gly Arg Ile Val Leu Ser
            215                 220                 225

GGG AAG CCG GCA ATT ATA CCT GAC AGG GAG GTT CTC TAC CAG GAG      720
Gly Lys Pro Ala Ile Ile Pro Asp Arg Glu Val Leu Tyr Gln Glu
            230                 235                 240

TTC GAT GAG ATG GAA GAG AAG GAG ACA GAG                          750
Phe Asp Glu Met Glu Glu Lys Glu Thr Glu
            245                 250
```

( 2 ) INFORMATION FOR SEQ ID NO:11:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 11:

GATCACCGGT CTAGATCT            18

( 2 ) INFORMATION FOR SEQ ID NO:12:

( i ) SEQUENCE CHARACTERISTICS:

( A ) LENGTH: 28 bases
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY:

( x i ) SEQUENCE DESCRIPTION: SEQ ID NO: 12:

CCGGTCCGGA AGAAAAAGAG ACGCTAGC                                          28

( 2 ) INFORMATION FOR SEQ ID NO:13:

( i ) SEQUENCE CHARACTERISTICS:
( A ) LENGTH: 79 bases
( B ) TYPE: nucleic acid
( C ) STRANDEDNESS: singel
( D ) TOPOLOGY: linear ( i i ) MOLECULE TYPE: cDNA ( i x ) FEATURE:
( A ) NAME/KEY:

( x i ) SEQUENCE DESCRIPTION: SEQ ID NO: 13:

CCGGCAATTA TACCTGACAG GGAGGTTCTC TACCAGGAAT TCGATGAGAT GGAAGAGTGC        60

CGGAAGAAAA AGAGACGCA                                                    79

( 2 ) INFORMATION FOR SEQ ID NO:14:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: polypeptide ( i x ) FEATURE:
( A ) NAME/KEY: NS4A Active Mutant ( x i ) SEQUENCE DESCRIPTION: SEQ ID NO: 14:

Gly Cys Val Val Ile Val Gly Arg Ile Val Leu Ser Gly Lys
5 10

( 2 ) INFORMATION FOR SEQ ID NO:15:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: polypeptide ( i x ) FEATURE:
( A ) NAME/KEY: NS4A Active Mutant ( x i ) SEQUENCE DESCRIPTION: SEQ ID NO: 15:

Cys Val Val Ile Val Gly Arg Ile Val Leu Ser Gly Lys
5 10

( 2 ) INFORMATION FOR SEQ ID NO:16:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: polypeptide ( i x ) FEATURE:
    ( A ) NAME/KEY: Soluble 5A/5B Substrate ( x i ) SEQUENCE DESCRIPTION: SEQ ID NO: 16:

Asp Thr Glu Asp Val Val Cys Cys Ser Met Ser Tyr Thr Trp Thr
               5                         10                     15

Gly Lys ( 2 ) INFORMATION FOR SEQ ID NO:17:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: polypeptide ( i x ) FEATURE:
        ( A ) NAME/KEY: Mutant 5A/5B Substrate ( x i ) SEQUENCE DESCRIPTION: SEQ ID NO: 17:

Asp Thr Glu Asp Val Val Ala Cys Ser Met Ser Tyr Thr Trp Thr
               5                         10                     15

Gly ( 2 ) INFORMATION FOR SEQ ID NO:18:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: polypeptide ( i x ) FEATURE:
        ( A ) NAME/KEY: Mutant Soluble 5A/5B Substrate ( x i ) SEQUENCE DESCRIPTION: SEQ ID NO: 18:

Asp Thr Glu Asp Val Val Ala Cys Ser Met Ser Tyr Thr Trp Thr
               5                         10                     15

Gly Lys ( 2 ) INFORMATION FOR SEQ ID NO:19:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: polypeptide ( i x ) FEATURE:
        ( A ) NAME/KEY: Soluble 5A/5B Substrate ( x i ) SEQUENCE DESCRIPTION: SEQ ID NO: 19:

Asp Thr Glu Asp Val Val Cys Cys Ser Met Ser Tyr Thr Trp Thr
               5                         10                     15

Gly Lys Tyr ( 2 ) INFORMATION FOR SEQ ID NO:20:

( i ) SEQUENCE CHARACTERISTICS:

(A) LENGTH: 18 amino acids
(B) TYPE: amino acid
(C) STRANDEDNESS: single
(D) TOPOLOGY: linear (ii) MOLECULE TYPE: polypeptide (ix) FEATURE:
(A) NAME/KEY: Soluble 5A/5B Substrate (xi) SEQUENCE DESCRIPTION: SEQ ID NO: 20:

Asp Thr Glu Asp Val Val Ala Cys Ser Met Ser Tyr Thr Trp Thr
                    5                   10                  15
Gly Lys Tyr (2) INFORMATION FOR SEQ ID NO:21:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: polypeptide (ix) FEATURE:
(A) NAME/KEY: Soluble 4B/5A Substrate (xi) SEQUENCE DESCRIPTION: SEQ ID NO: 21:

Trp Ile Ser Ser Glu Cys Thr Thr Pro Cys Ser Gly Ser Trp Leu
                    5                   10                  15
Arg Asp Ile Trp Asp
                20

(2) INFORMATION FOR SEQ ID NO:22:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: polypeptide (ix) FEATURE:
(A) NAME/KEY: histidine tag (xi) SEQUENCE DESCRIPTION: SEQ ID NO: 22:

Met Arg Gly Ser His His His His His His Thr Asp Pro
                    5                   10

(2) INFORMATION FOR SEQ ID NO:23:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: polypeptide (ix) FEATURE:
(A) NAME/KEY: hydrophilic tail (xi) SEQUENCE DESCRIPTION: SEQ ID NO: 23:

Arg Lys Lys Lys Arg Arg Lys Leu Asn
                    5

(2) INFORMATION FOR SEQ ID NO:24:

( i ) SEQUENCE CHARACTERISTICS:
　　　　( A ) LENGTH: 4 amino acids
　　　　( B ) TYPE: amino acid
　　　　( C ) STRANDEDNESS: single
　　　　( D ) TOPOLOGY: linear ( i i ) MOLECULE TYPE: polypeptide ( i x ) FEATURE:
　　　　( A ) NAME/KEY: hydrophilic tail ( x i ) SEQUENCE DESCRIPTION: SEQ ID NO: 24:

Lys　Glu　Thr　Glu ( 2 ) INFORMATION FOR SEQ ID NO:25:

( i ) SEQUENCE CHARACTERISTICS:
　　　　( A ) LENGTH: 20 amino acids
　　　　( B ) TYPE: amino acid
　　　　( C ) STRANDEDNESS: single
　　　　( D ) TOPOLOGY: linear ( i i ) MOLECULE TYPE: polypeptide ( i x ) FEATURE:
　　　　( A ) NAME/KEY: hydrophilic tail ( x i ) SEQUENCE DESCRIPTION: SEQ ID NO: 25:

Trp　Ile　Ser　Ser　Glu　Cys　Thr　Thr　Pro　Cys　Ser　Gly　Ser　Trp　Leu
Arg　Asp　Ile　Trp　Asp
　　　　　　　　20

( 2 ) INFORMATION FOR SEQ ID NO:26:

( i ) SEQUENCE CHARACTERISTICS:
　　　　( A ) LENGTH: 153 base pairs
　　　　( B ) TYPE: nucleic acid
　　　　( C ) STRANDEDNESS: single
　　　　( D ) TOPOLOGY: linear ( i i ) MOLECULE TYPE: cDNA ( i x ) FEATURE:
　　　　( A ) NAME/KEY: NS4A Mutant ( x i ) SEQUENCE DESCRIPTION: SEQ ID NO: 26:

| GTG | CTC | GTT | GGC | GGC | GTC | CTG | GCT | GCT | CTG | GCC | GCG | TAT | TGC | CTG | 4 |
|-----|-----|-----|-----|-----|-----|-----|-----|-----|-----|-----|-----|-----|-----|-----|---|
| Val | Leu | Val | Gly | Gly | Val | Leu | Ala | Ala | Leu | Ala | Ala | Tyr | Cys | Leu | |
| 1   |     |     |     | 5   |     |     |     |     | 10  |     |     |     |     | 15  |

( x i ) SEQUENCE DESCRIPTION: SEQ ID NO: 27:

```
ATG AGA GGA TCG CAT CAC CAT CAC CAT CAC ACG GAT CCG CCC ATC       45
Met Arg Gly Ser His His His His His His Thr Asp Pro Pro Ile
              5                   10                  15

ACG GCG TAC GCC CAG CAG ACG AGA GGC CTC CTA GGG TGT ATA ATC       90
Thr Ala Tyr Ala Gln Gln Thr Arg Gly Leu Leu Gly Cys Ile Ile
             20                  25                  30

ACC AGC CTG ACT GGC CGG GAC AAA AAC CAA GTG GAG GGT GAG GTC      135
Thr Ser Leu Thr Gly Arg Asp Lys Asn Gln Val Glu Gly Glu Val
             35                  40                  45

CAG ATC GTG TCA ACT GCT ACC CAA ACC TTC CTG GCA ACG TGC ATC      180
Gln Ile Val Ser Thr Ala Thr Gln Thr Phe Leu Ala Thr Cys Ile
             50                  55                  60

AAT GGG GTA TGC TGG ACT GTC TAC CAC GGG GCC GGA ACG AGG ACC      225
Asn Gly Val Cys Trp Thr Val Tyr His Gly Ala Gly Thr Arg Thr
             65                  70                  75

ATC GCA TCA CCC AAG GGT CCT GTC ATC CAG ATG TAT ACC AAT GTG      270
Ile Ala Ser Pro Lys Gly Pro Val Ile Gln Met Tyr Thr Asn Val
             80                  85                  90

GAC CAA GAC CTT GTG GGC TGG CCC GCT CCT CAA GGT TCC CGC TCA      315
Asp Gln Asp Leu Val Gly Trp Pro Ala Pro Gln Gly Ser Arg Ser
             95                  100                 105

TTG ACA CCC TGC ACC TGC GGC TCC TCG GAC CTT TAC CTG GTT ACG      360
Leu Thr Pro Cys Thr Cys Gly Ser Ser Asp Leu Tyr Leu Val Thr
             110                 115                 120

AGG CAC GCC GAC GTC ATT CCC GTG CGC CGG CGA GGT GAT AGC AGG      405
Arg His Ala Asp Val Ile Pro Val Arg Arg Arg Gly Asp Ser Arg
             125                 130                 135

GGT AGC CTG CTT TCG CCC CGG CCC ATT TCC TAC CTA AAA GGC TCC      450
Gly Ser Leu Leu Ser Pro Arg Pro Ile Ser Tyr Leu Lys Gly Ser
             140                 145                 150

TCG GGG GGT CCG CTG TTG TGC CCC GCG GGA CAC GCC GTG GGC CTA      495
Ser Gly Gly Pro Leu Leu Cys Pro Ala Gly His Ala Val Gly Leu
             155                 160                 165

TTC AGG GCC GCG GTG TGC ACC CGT GGA GTG ACC AAG GCG GTG GAC      540
Phe Arg Ala Ala Val Cys Thr Arg Gly Val Thr Lys Ala Val Asp
             170                 175                 180

TTT ATC CCT GTG GAG AAC CTA GAG ACA ACC ATG AGA TCC CCG GGG      585
Phe Ile Pro Val Glu Asn Leu Glu Thr Thr Met Arg Ser Pro Gly
             185                 190                 195

GTG CTC GTT GGC GGC GTC CTG GCT GCT CTG GCC GCG TAT TGC CTG      630
Val Leu Val Gly Gly Val Leu Ala Ala Leu Ala Ala Tyr Cys Leu
             200                 205                 210

TCA ACA GGC TGC GTG GTC ATA GTG GGC AGG ATT GTC TTG TCC GGG      675
Ser Thr Gly Cys Val Val Ile Val Gly Arg Ile Val Leu Ser Gly
             215                 220                 225

AAG CCG GCA ATT ATA CCT GAC AGG GAG GTT CTC TAC CAG GAG TTC      720
Lys Pro Ala Ile Ile Pro Asp Arg Glu Val Leu Tyr Gln Glu Phe
             230                 235                 240

GAT GAG ATG GAA GAG TGC CGG AAG AAA AAG AGA CGC AAG CTT AAT      765
Asp Glu Met Glu Glu Cys Arg Lys Lys Lys Arg Arg Lys Leu Asn
             245                 250                 255
```

( 2 ) INFORMATION FOR SEQ ID NO:28:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: Native NS4A ( x i ) SEQUENCE DESCRIPTION: SEQ ID NO: 28:

| TCA | ACA | TGG | GTG | CTC | GTT | GGC | GGC | GTC | CTG | GCT | GCT | CTG | GCC | GCG | 45 |
|---|---|---|---|---|---|---|---|---|---|---|---|---|---|---|---|
| Ser | Thr | Trp | Val | Leu | Val | Gly | Gly | Val | Leu | Ala | Ala | Leu | Ala | Ala | |
| 1 | | | | 5 | | | | | 10 | | | | | 15 | |

| TAT | TGC | CTG | TCA | ACA | GGC | TGC | GTG | GTC | ATA | GTG | GGC | AGG | ATT | GTC | 90 |
|---|---|---|---|---|---|---|---|---|---|---|---|---|---|---|---|
| Tyr | Cys | Leu | Ser | Thr | Gly | Cys | Val | Val | Ile | Val | Gly | Arg | Ile | Val | |
| | | | 20 | | | | | 25 | | | | | 30 | | |

| TTG | TCC | GGG | AAG | CCG | GCA | ATT | ATA | CCT | GAC | AGG | GAG | GTT | CTC | TAC | 135 |
|---|---|---|---|---|---|---|---|---|---|---|---|---|---|---|---|
| Leu | Ser | Gly | Lys | Pro | Ala | Ile | Ile | Pro | Asp | Arg | Glu | Val | Leu | Tyr | |
| | | | | 35 | | | | | 40 | | | | | 45 | |

| CAG | GAG | TTC | GAT | GAG | ATG | GAA | GAG | TGC | 162 |
|---|---|---|---|---|---|---|---|---|---|
| Gln | Glu | Phe | Asp | Glu | Met | Glu | Glu | Cys | |
| | | | | 50 | | | | | |

( 2 ) INFORMATION FOR SEQ ID NO:29:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: Native NS4A ( x i ) SEQUENCE DESCRIPTION: SEQ ID NO: 29:

| TCA | ACA | TGG | GTG | CTC | GTT | GGC | GGC | GTC | CTG | GCT | GCT | CTG | GCC | GCG | 45 |
|---|---|---|---|---|---|---|---|---|---|---|---|---|---|---|---|
| Ser | Thr | Trp | Val | Leu | Val | Gly | Gly | Val | Leu | Ala | Ala | Leu | Ala | Ala | |
| 1 | | | | 5 | | | | | 10 | | | | | 15 | |

| TAT | TGC | CTG | TCA | ACA | GGC | TGC | GTG | GTC | ATA | GTG | GGC | AGG | ATT | GTC | 90 |
|---|---|---|---|---|---|---|---|---|---|---|---|---|---|---|---|
| Tyr | Cys | Leu | Ser | Thr | Gly | Cys | Val | Val | Ile | Val | Gly | Arg | Ile | Val | |
| | | | 20 | | | | | 25 | | | | | 30 | | |

| TTG | TCC | GGG | AAG | CCG | GCA | ATT | ATA | CCT | GAC | AGG | GAG | GTT | CTC | TAC | 135 |
|---|---|---|---|---|---|---|---|---|---|---|---|---|---|---|---|
| Leu | Ser | Gly | Lys | Pro | Ala | Ile | Ile | Pro | Asp | Arg | Glu | Val | Leu | Tyr | |
| | | | | 35 | | | | | 40 | | | | | 45 | |

| CAG | GAG | TTC | GAT | GAG | ATG | GAA | GAG | TGC | 162 |
|---|---|---|---|---|---|---|---|---|---|
| Gln | Glu | Phe | Asp | Glu | Met | Glu | Glu | Cys | |
| | | | | 50 | | | | | |

( 2 ) INFORMATION FOR SEQ ID NO:30:

( i ) SEQUENCE CHARACTERISTICS:
        ( A ) LENGTH: 33 amino acid residues
        ( B ) TYPE: amino acid
        ( C ) STRANDEDNESS: single
        ( D ) TOPOLOGY: linear ( i i ) MOLECULE TYPE: polypeptide ( i x ) FEATURE:
    ( A ) NAME/KEY: Carboxl 33 mer of NS4A ( x i ) SEQUENCE DESCRIPTION: SEQ ID NO: 30:

| Cys | Val | Val | Ile | Val | Gly | Arg | Ile | Val | Leu | Ser | Gly | Lys | Pro | Ala |
|---|---|---|---|---|---|---|---|---|---|---|---|---|---|---|
| 1 | | | | 5 | | | | | 10 | | | | | 15 |

| Ile | Ile | Pro | Asp | Arg | Glu | Val | Leu | Tyr | Gln | Glu | Phe | Asp | Glu | Met |
|---|---|---|---|---|---|---|---|---|---|---|---|---|---|---|
| | | | | 20 | | | | | 25 | | | | | 30 |

| Glu | Glu | Cys |
|---|---|---|

( 2 ) INFORMATION FOR SEQ ID NO:31:

( i ) SEQUENCE CHARACTERISTICS:
        ( A ) LENGTH: 33 amino acid residues
        ( B ) TYPE: amino acid
        ( C ) STRANDEDNESS: single
        ( D ) TOPOLOGY: linear ( i i ) MOLECULE TYPE: polypeptide ( i x ) FEATURE:
        ( A ) NAME/KEY: Carboxl 33 mer of NS4A of HCV-BK strain ( x i ) SEQUENCE DESCRIPTION: SEQ ID NO: 31:

```
Ser Val Val Ile Val Gly Arg Ile Ile Leu Ser Gly Arg Pro Ala
 1           5                   10                  15
Ile Val Pro Asp Arg Glu Leu Leu Tyr Gln Glu Phe Asp Glu Met
             20                  25                  30
Glu Glu Cys
```

( 2 ) INFORMATION FOR SEQ ID NO:32:

( i ) SEQUENCE CHARACTERISTICS:
        ( A ) LENGTH: 14 bases
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: yes ( i x ) FEATURE:
        ( D ) OTHER INFORMATION: Antisense strand of SEQ ID NO: 11:

( x i ) SEQUENCE DESCRIPTION: SEQ ID NO: 32:

TGGCCAGATC TAGA    14

( 2 ) INFORMATION FOR SEQ ID NO:33:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: yes ( i x ) FEATURE:
        ( D ) OTHER INFORMATION: Antisense strand of SEQ ID NO: 12:

( x i ) SEQUENCE DESCRIPTION: SEQ ID NO: 33:

AGGCCTTCTT TTTCTCTGCG ATCG    24

( 2 ) INFORMATION FOR SEQ ID NO:34:

( i ) SEQUENCE CHARACTERISTICS:
        ( A ) LENGTH: 79 bases
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: yes ( i x ) FEATURE:
        ( D ) OTHER INFORMATION: Antisense strand of SEQ ID NO: 13:

( x i ) SEQUENCE DESCRIPTION: SEQ ID NO: 34:

-continued

| | | | | | | |
|---|---|---|---|---|---|---|
| GTTAATATGG | ACTGTCCCTC | CAAGAGATGG | TCCTTAAGCT | ACTCTACCTT | CTCACGGCCT | 60 |
| TCTTTTTCTC | TGCGTTCGA | | | | | 79 |

SOLUBLE ACTIVE HEPATITIS C VIRUS PROTEASE

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world. The viral infection accounts for greater than 90% of transfusion -associated hepatitis in U.S. and it is the predominant form of hepatitis in adults over 40 years of age. Almost all of the infections result in chronic hepatitis and nearly 20% develop liver cirrhosis.

The virus particle has not been identified due to the lack of an efficient in vitro replication system and the extremely low amount of HCV particles in infected liver tissues or blood. However, molecular cloning of the viral genome has been accomplished by isolating the messenger RNA (mRNA) from the serum of infected chimpanzees then cloned using recombinant methodologies. [Grakoui A. et al. *J. Virol.* 67: 1385–1395 (1993)] It is now known that HCV contains a positive strand RNA genome comprising approximately 9400 nucleotides, whose organization is similar to that of flaviviruses and pestiviruses. The genome of HCV, like that of flavi- and pestiviruses, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least nine mature viral proteins are produced from the polyprotein by specific proteolysis. The order and nomenclature of the cleavage products are as follows: $NH_2$-C-E1-E2-NS2-NS3-NS4A-NS4B-NS5A-NS5B-COOH. (FIG. 1). The three amino terminal putative structural proteins, C (capsid), E1, and E2 ( two envelope glycoproteins), are believed to be cleaved by host signal peptidases of the endoplasmic reticulum(ER). The host enzyme is also responsible for generating the amino terminus of NS2. The proteolytic processing of the nonstructural proteins are carried out by the viral proteases: NS2–3 and NS3, contained within the viral polyprotein. The NS2–3 protease catalyzes the cleavage between NS2 and NS3. It is a metalloprotease and requires both NS2 and the protease domain of NS3. The NS3 protease catalyzes the rest of the cleavages in the nonstructural part of the polyprotein. The NS3 protein contains 631 amino acid residues and is comprised of two enzymatic domains: the protease domain contained within amino acid residues 1–181 and a helicase ATPase domain contained within the rest of the protein. It is not known if the 70 kD NS3 protein is cleaved further in infected cells to separate the protease domain from the helicase domain, however, no cleavage has been observed in cell culture expression studies.

The NS3 protease is a member of the serine class of enzymes. It contains His, Asp, and Ser as the catalytic triad, Ser being the active site residue. Mutation of the Ser residue abolishes the cleavages at substrates NS3/4A, NS4A/4B, NS4B/5A, and NS5A/5B. The cleavage between NS3 and NS4A is intramolecular, whereas the cleavages at NS 4A/4B, 4B/5A, 5A/5B sites occur in trans.

Experiments using transient expression of various forms of HCV NS polyproteins in mammalian cells have established that the NS3 serine protease is necessary but not sufficient for efficient processing of all these cleavages. Like flaviviruses, the HCV NS3 protease also requires a cofactor to catalyze some of these cleavage reactions. In addition to the serine protease NS3, the NS4A protein is absolutely required for the cleavage of the substrate at the 4B/5A site and increases the efficiency of cleavage of the substrate between 5A/5B, and possibly 4A/4B.

Because the HCV NS3 protease cleaves the non-structural HCV proteins which are necessary for the HCV replication, the NS3 protease can be a target for the development of therapeutic agents against the HCV virus. The gene encoding the HCV NS3 protein has been cloned as disclosed in U.S. Pat. No. 5,371,017, however, the protein has not been produced in a soluble active form. If the HCV protease is to be useful as a target in a screen to discover therapeutic agents, the protease must be produced in a soluble active form. Thus, there is a need for a soluble active form of the HCV protease which can be produced in large quantities to be used in high throughput screen to detect inhibitors of the protease and for structural studies.

SUMMARY OF THE INVENTION

The present invention fills this need by providing for a soluble, active NS3 protease. In one embodiment of the present invention, the soluble NS3 protease is contained within a fusion protein comprised of a HCV protease fused to a solubilizing motif.

The present invention further provides for a soluble fusion protein comprised of the catalytic domain of the NS3 protease, cofactor domain of cofactor NS4A and a solubilizing motif wherein the NS4A cofactor has been mutated so that the NS3 protease and NS4A cofactor are not cleaved by the catalytic activity of the NS3 protease.

The present invention further provides for an HCV NS3 protease having a polypeptide comprising three or more histidine residues fused to the protease. This enables rapid purification of the protease.

The present invention provides further for a soluble HCV NS3 protease selected from the group consisting of SEQ ID NO 3, SEQ ID NO 4, SEQ ID NO: 5 SEQ ID NO 7, SEQ ID NO 8, SEQ ID NO 9, SEQ ID NO 10 and SEQ ID NO 27.

The present invention further provides for isolated nucleic acids and vectors which encode the HCV proteases of the present invention, host cells transformed or transfected by said nucleic acids or vectors. Also claimed is a method for making a soluble HCV protease comprising culturing the transformed or transfected host cell under conditions in which the nucleic acid or vector is expressed:

The present invention further provides for a host cell transformed or transfected with a nucleic acid or vector able to express soluble HCV NS3 protease, wherein the soluble HCV NS3 protease which is expressed is at least 1%, 2%, 3%, 4%, 5% or more of the total protein expressed by the cell.

DETAILED DESCRIPTION OF THE INVENTION

Figure 1:
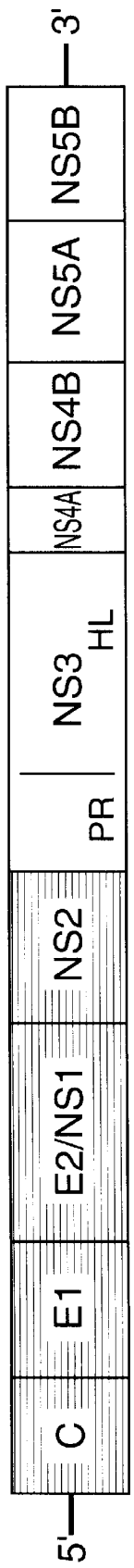
FIG. 1 schematically depicts the HCV genome.

The teachings of all references cited are incorporated herein in their entirety by reference.

The present invention is the production of the HCV NS3 protease in a soluble form. The HCV NS3 protease must be in a soluble form to be used in a screen to detect compounds which inhibit the protease from cleaving it's target substrate. We have discovered that if a peptide containing a solubilizing motif is attached to either the NS3 protease, preferably to the carboxyl terminus, the NS3 protease becomes readily soluble.

The amino acid sequence of the NS3 protease catalytic domain is shown in SEQ ID NO: 1. Prior to the present invention the NS3 protease was not expressed in a cell in a soluble form in sufficient quantities for extraction and purification. Moreover, soluble HCV NS3 protease was not able to be produced in soluble form in bacteria. This is important because bacterial expression is the preferred method of expression of large quantities of HCV protease. Soluble HCV NS3 protease of the present invention can be produced in several ways. A solubilizing motif can be fused to the protein resulting in a soluble protein. A solubilizing motif is any chemical moiety bound to the HCV NS3 protease which results in the NS3 protease becoming soluble in a buffered solution. Examples of such solubilizing motifs are chains of amino acids having polar side chains, preferably positively charged amino acids. The chain of amino adds should be about 4–10 amino acid residues in length. The preferred amino acids are arginine and lysine. Another example of a solubilizing motif is an amphipathic moiety. The solubilizing motif can be fused to either the amino terminus or carboxy terminus of the NS3 protease. A sequence which has been successfully fused to the carboxyl terminus to produce soluble NS3 protease is -Arg - Lys - Lys - Lys - Arg - Arg- (SEQ ID NO: 2). This has been fused to the carboxyl end of the NS3 protease to produce the polypeptides of SEQ ID NO: 3, SEQ ID NO: 4, SEQ ID NO: 8 and SEQ ID NO: 27. Other examples of soluble HCV NS3 protease having a hydrophilic amino acid residue tail which were made are SEQ ID NO: 9, and SEQ ID NO: 10.

In another embodiment of the present invention, soluble HCV NS3 protease can also be produced which does not have a solubilizing motif as for example the proteases shown in SEQ ID NO: 1 and SEQ ID NO: 7. Preferably the NS3 protease will have a histidine tag fused to its amino acid terminus for use in purifying the protein on a nickel ($Ni^{2+}$) coated resin. See SEQ ID NO: 5. In this embodiment the protease is produced as insoluble aggregates or as inclusion bodies in bacteria such as in *E. coli*.

The insoluble HCV NS3 protease is first extracted from the bacteria by homogenization or sonication of the bacteria. The aggregates containing the bacteria are then solubilized in a 5M solution of guanidine hydrochloride (GuHC1). The NS3 protease is then purified from high molecular weight aggregates by size exclusion chromatography, as for example by applying the solution to a SEPHACRYL S-300 size exclusion gel column. Fractions containing the NS3 protease in 5M GuCl are pooled and diluted to about 0.1M GuHCl in a refolding buffer comprised of dithiothreitol and lauryl maltoside.

The diluted solution is then applied to a reverse phase chromatography column and pools containing the NS3 protease collected. The pH of the protease fractions is then raised in a stepwise manner to about 7.4 so as to produce properly refolded soluble, active NS3 protease.

It has also been discovered that the HCV NS3 protease is much more effective in cleaving the HCV non-structural proteins, if the co-factor NS4A protein is present (SEQ ID NO: 6). Accordingly, the present invention is also comprised of a fusion of the NS4A cofactor domain protein with the NS3 protease, in particular the fusion of the NS3 protease and the NS4A cofactor wherein the NS4A is mutated such the NS3 protease and the NS4A cofactor is not cleaved by the NS3 protease. Examples of the fused NS3 and NS4A constructs are shown in SEQ ID NOs. 7,8,9, 10 and 27.

DNA encoding the NS3 protease of this invention can be prepared by chemical synthesis using the known nucleic acid sequence [Ratner et al., *Nucleic Acids Res.* 13:5007 (1985)] and standard methods such as the phosphoramidite solid support method of Matteucci et al. [*J Am. Chem. Soc.* 103:3185 (1981)] or the method of Yoo et al. [*J. Biol. Chem.* 764:17078 (1989)]. See also Glick, Bernard R. and Pasternak, *Molecular Biotechnology*: pages 55–63, (ASM Press, Washington, D.C. 1994). The gene encoding the protease can also be obtained using the plasmid disclosed in Grakoui, A., Wychowski, C., Lin, C., Feinstone, S. M., and Rice, C. M., Expression and Identification of Hepatitis C Virus polyprotein Cleavage Products, *J. Virol* 67;1385–1395 (1993). Also, the nucleic acid encoding HCV protease can be isolated, amplified and cloned (from patients infected with the HCV virus). Furthermore, the HCV genome has been disclosed in PCT WO 89/04669 and are available from the American Type Culture Collection (ATCC), 12301 Parklawn Drive, Rockville, Md. under ATCC accession no. 40394.

Of course, because of the degeneracy of the genetic code, there are many functionally equivalent nucleic acid sequences that can encode mature human HCV protease as defined herein. Such functionally equivalent sequences, which can readily be prepared using known methods such as chemical synthesis, PCR employing modified primers and site-directed mutagenesis, are within the scope of this invention.

Various expression vectors can be used to express DNA encoding HCV NS3 protease. Conventional vectors used for expression of recombinant proteins used for expression of recombinant proteins in prokaryotic or eukaryotic cells may be used. Preferred vectors include the pcD vectors described by Okayama et al., *Mol. Cell. Bio.* 3: 280–289 (1983); and Takebe et al., *Mol. Cell. Biol.* 8: 466–472 (1988). Other SV40-based mammalian expression vectors include those disclosed in Kaufman et al., *Mol. Cell. Biol.* 2: 1304–1319 (1982) and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of the polypeptide. Eukaryotic cell lines include mammalian, yeast and insect cell lines. Exemplary mammalian cell lines include COS-7 cells, mouse L cells and Chinese Hamster Ovary (CHO) cells. See Sambrook et al., supra and Ausubel et al., supra.

As used herein, the term "transformed bacteria" means bacteria that have been genetically engineered to produce a mammalian protein. Such genetic engineering usually entails the introduction of an expression vector into a bacterium. The expression vector is capable of autonomous replication and protein expression relative to genes in the bacterial genome. Construction of bacterial expression is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.* 83:599 (1986), Sproat et al., *Nucleic Acid Research* 13:2959 (1985) and Mullenbach et al., *J. Biol. Chem* 261:719 (1986) disclose how to construct synthetic genes for expression in bacteria. Many bacterial expression vectors are available commercially and through the American Type Culture Collection (ATCC), Rockville, Md.

Insertion of DNA encoding human HCV protease into a vector is easily accomplished when the termini of both the DNA and the vector comprise the same restriction site. If this is not the case, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Many *E. coli*-compatible expression vectors can be used to produce soluble HCV NS3 protease of the present invention, including but not limited to vectors containing bacterial or bacteriophage promoters such as the Tac, Lac, Trp, LacUV5, 1 $P_r$ and 1 $P_L$ promoters. Preferably, a vector selected will have expression control sequences that permit regulation of the rate of HCV protease expression. Then, HCV protease production can be regulated to avoid overproduction that could prove toxic to the host cells. Most preferred is a vector comprising, from 5' to 3' (upstream to downstream), a Tac promoter, a lac Iq repressor gene and DNA encoding mature human HCV protease. The vectors chosen for use in this invention may also encode secretory leaders such as the ompA or protein A leader, as long as such leaders are cleaved during post-translational processing to produce mature HCV protease or if the leaders are not cleaved, the leaders do not interfere with the enzymatic activity of the protease.

Fusion peptides will typically be made by either recombinant nudeic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, NY. Techniques for synthesis of polypeptides are described, e.g., in Merrifield (1963) *J. Amer. Chem. Soc.* 85:2149–2156; Merrifield (1986) *Science* 232: 341–347; and Stewart et al (1984)., "*Solid Phase Peptide Synthesis*"(2nd Edition), Pierce Chemical Co., Rockford, Ill.; and Atherton, et al. (1989) *Solid Phase Peptide Synthesis: A Practical Approach*, IRL Press, Oxford; and Grant (1992) *Synthetic Peptides: A User's Guide*, W. H. Freeman, NY.

The smaller peptides such as the NS4A cofactor and the substrates 5A/5B and 4B/5A can be synthesized by a suitable method such as by exclusive solid phase synthesis, partial solid phase methods, fragment condensation or classical solution synthesis. The polypeptides are preferably prepared by solid phase peptide synthesis as described by Merrifield, J. Am. Chem. Soc. 85:2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [eg., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cydohexyloxycarbonyl] and alkyl type protecting groups (e.g. benzyl, triphenylmethyl). The preferred protecting groups are tBoc and Fmoc, thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. In Fmoc chemistry, they are mostly tert.-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl for Trp and 2-bromobenzyl for Tyr. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for Arg, trityl for Asn, Cys, Gln and His, tert. butyl for Asp, Glu, Ser, Thr and Tyr, tBoc for Lys and Trp.

For the synthesis of phosphopeptides, either direct or post-assembly incorporation of the phosphate group is used. In the direct incorporation strategy, the phosphate group on Ser, Thr or Tyr may be protected by methyl, benzyl or tert.butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl group of Ser, Thr or Tyr was derivatized on solid phase with di-tert.butyl-, dibenzyl- or dimethyl-N,N'-diisopropylphosphoramidite and then oxidized by tert.butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al (1984)., "Solid Phase Peptide Synthesis" (2nd Edition), Pierce Chemical Co., Rockford, Ill.; and Bayer & Rapp (1986) Chem. Pept. Prot. 3,3; and Atherton, et al. (1989) Solid Phase Peptide Synthesis: A Practical Approach, IRL Press, Oxford.

The C-terminal amino acid, protected at the side-chain if necessary and at the alpha-amino group, is attached to a hydroxylmethyl resin using various activating agents including dicydohexylcarbodiimide (DCC), N,N'-diisopropylcarbodiimide DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyluronium hexafluorophosphate (HBTU) and its tetrafluoroborate analog (TBTU) or its pyrrolidine analog (HBPyU), O-(7-azabenzotriazol-1-yl)-1,1,3,3-tetramethyluronium hexafluorophosphate (HATU) and its tetrafluoroborate analog (TATU) or pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino add is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g. by the ninhydrin reaction as described by Kaiser et al., Anal. Biochem. 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired polypeptide, the polypeptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury(II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

Recombinant DNA methodology can also be used to prepare the polypeptides. The known genetic code, tailored if desired with known preferred codons for more efficient expression in a given host organism, can be used to synthesize oligonucleotides encoding the desired amino acid sequences. The phosphoramidite solid support method of Matteucci et al. , J. Am. Chem. Soc. 103:3185 (1981) or other known methods can be used for such syntheses. The resulting oligonucleotides can be inserted into an appropriate vector and expressed in a compatible host organism.

The polypeptides of the invention can be purified using HPLC, gel filtration, ion exchange and partition chromatography, countercurrent distribution or other well known methods. In a preferred embodiment of the present invention the NS3 fusion proteins also contain a histidine tag which facilitates purification using a $Ni^+$ column as is illustrated below.

One can use the NS3 protease, the NS4 cofactor and the peptide substrates, either 4B/5A or 5A/5B, to develop high throughput assays. These can be used to screen for compounds which inhibit proteolytic activity of the protease. This is carried out by developing techniques for determining whether or not a compound will inhibit the NS3 protease from cleaving the viral substrates. Examples of such synthetic substrates are SEQ ID NOs 16, 17, 18, 19, 20 and 21. If the substrates are not cleaved, the virus cannot replicate. One example of such a high throughput assay is the scintillation proximity assay (SPA). SPA technology involves the use of beads coated with scintillant. Bound to the beads are acceptor molecules such as antibodies, receptors or enzyme substrates which interact with ligands or enzymes in a reversible manner.

For a typical protease assay the substrate peptide is biotinylated at one end and the other end is radiolabelled with low energy emitters such as $^{125}I$ or $^3H$. The labeled substrate is then incubated with the enzyme. Avidin coated SPA beads are then added which bind to the biotin. When the substrate peptide is cleaved by the protease, the radioactive emitter is no longer in proximity to the scintillant bead and no light emission takes place. Inhibitors of the protease will leave the substrate intact and can be identified by the resulting light emission which takes place in their presence.

Another type of protease assay, utilizes the phenomenon of surface plasmon resonance (SPR). A novel, high throughput enzymatic assay utilizing surface plasmon resonance technology has been successfully developed. Using this assay, and a dedicated BIAcore™ instrument, at least 1000 samples per week can be screened for either their enzymatic activity or their inhibitory effects toward the enzymatic activity, in a 96 well plate format. This methodology is readily adaptable to any enzyme-substrate reaction. The advantage of this assay over the SPA assay is that it does not require a radiolabeled peptide substrate.

The following examples are included to illustrate the present invention but not to limit it.

EXAMPLES 1

Production of HCV NS3 Protease

A. Plasmid Constructions

Figure 2:
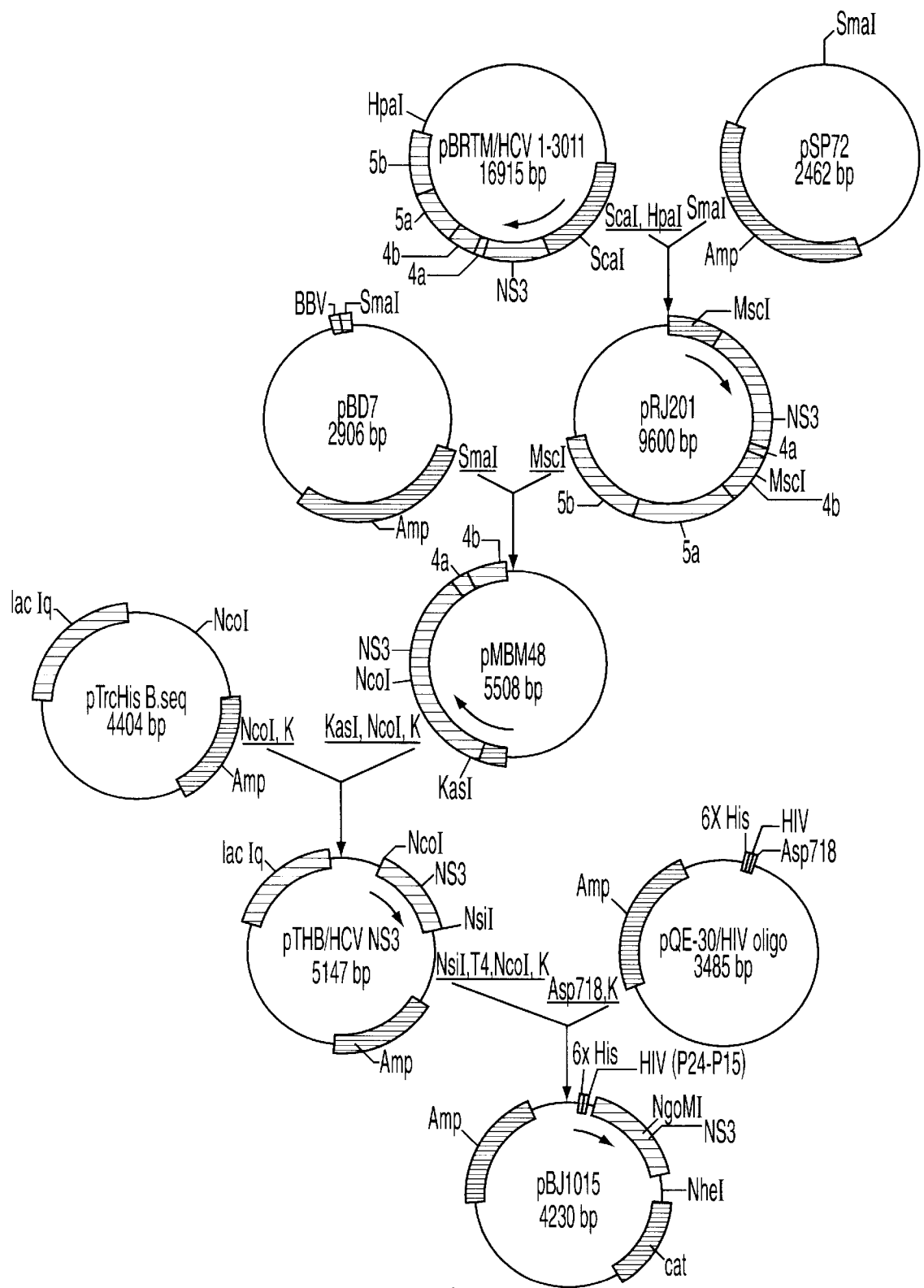
FIG. 2 depicts the recombinant synthesis of plasmid pBJ1015.
Figure 3:
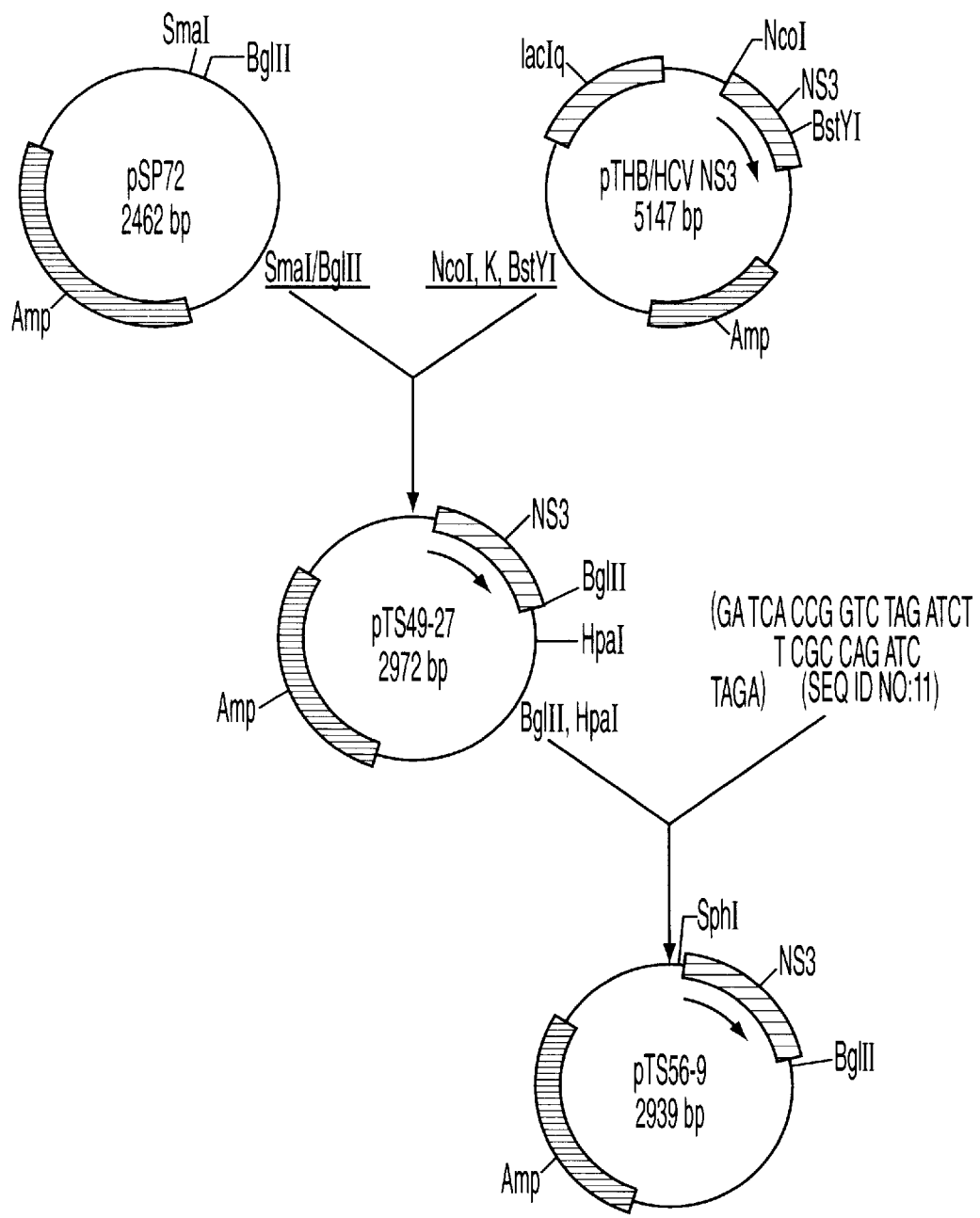
FIG. 3 depicts the recombinant synthesis of plasmid pTS56-9.

Several plasmids were designed and constructed using standard recombinant DNA techniques (Sambrook,Fritsch & Maniatis) to express the HCV protease in *E. coli* (FIG. 2–7). All HCV specific sequences originated from the parental plasmid pBRTM/HCV 1–3011 (Grakoui et al.1993). To express the N-terminal 183 amino acid versions of the protease, a stop codon was inserted into the HCV genome using synthetic oligonucleotides (FIG. 3). The plasmids designed to express the N-terminal 246 amino acid residues were generated by the natural Nco1 restriction site at the C-terminus.

i) Construction of the plasmid pBJ1015 (FIG. 2)

The plasmid pBRTM/HCV 1–3011 containing the entire HCV genome (Grakoui A., et al., *J. Virol.* 67: 1385–1395) was digested with the restriction enzymes Sca I and Hpa I and the 7138 bp (base pair) DNA fragment was isolated and cloned to the Sma I site of pSP72 (Promega) to produce the plasmid,pRJ201. The plasmid pRJ 201 was digested with Msc I and the 2106 bp Msc I fragment was isolated and cloned into the Sma I site of the plasmid pBD7. The resulting plasmid pMBM48 was digested with Kas I and Nco I, and the 734 bp DNA fragment after blunt ending with Klenow polymerase was isolated and cloned into Nco I digested, klenow polymerase treated pTrc HIS B seq expression plasmid (Invitrogen). The ligation regenerated a Nco I site at the 5' end and Nsi I site at the 3' end of HCV sequence. The plasmid pTHB HCV NS3 was then digested with Nco I and Nsi I, and treated with klenow polymerase and T4 DNA polymerase, to produce a blunt ended 738 bp DNA fragment which was isolated and cloned into Asp I cut, klenow polymerase treated expression plasmid pQE30 (HIV). The resulting plasmid pBJ 1015 expresses HCV NS3 (246 amino acids) protease.

(ii) Construction of the plasmid pTS 56-9 with a stop codon after amino acid 183 (FIG. 3)

The plasmid pTHB HCV NS3 was digested with Nco I, treated with klenow polymerase, then digested with Bst Y I; and the DNA fragment containing HCV sequence was isolated and cloned into Sma I and Bgl II digested pSP72. The resulting plasmid pTS 49-27 was then digested with Bgl II and Hpa I and ligated with a double stranded oligonucleotide:

```
GA TCA CCG GTC TAG ATCT        (SEQ ID NO 11)
   T  GGC CAG ATC TAGA
``` to produce pTS 56-9.

Thus, a stop codon was placed directly at the end of DNA encoding the protease catalytic domain of the NS3 protein. This enabled the HCV protease to be expressed independently from the helicase domain of the NS3 protein.

Figure 4:
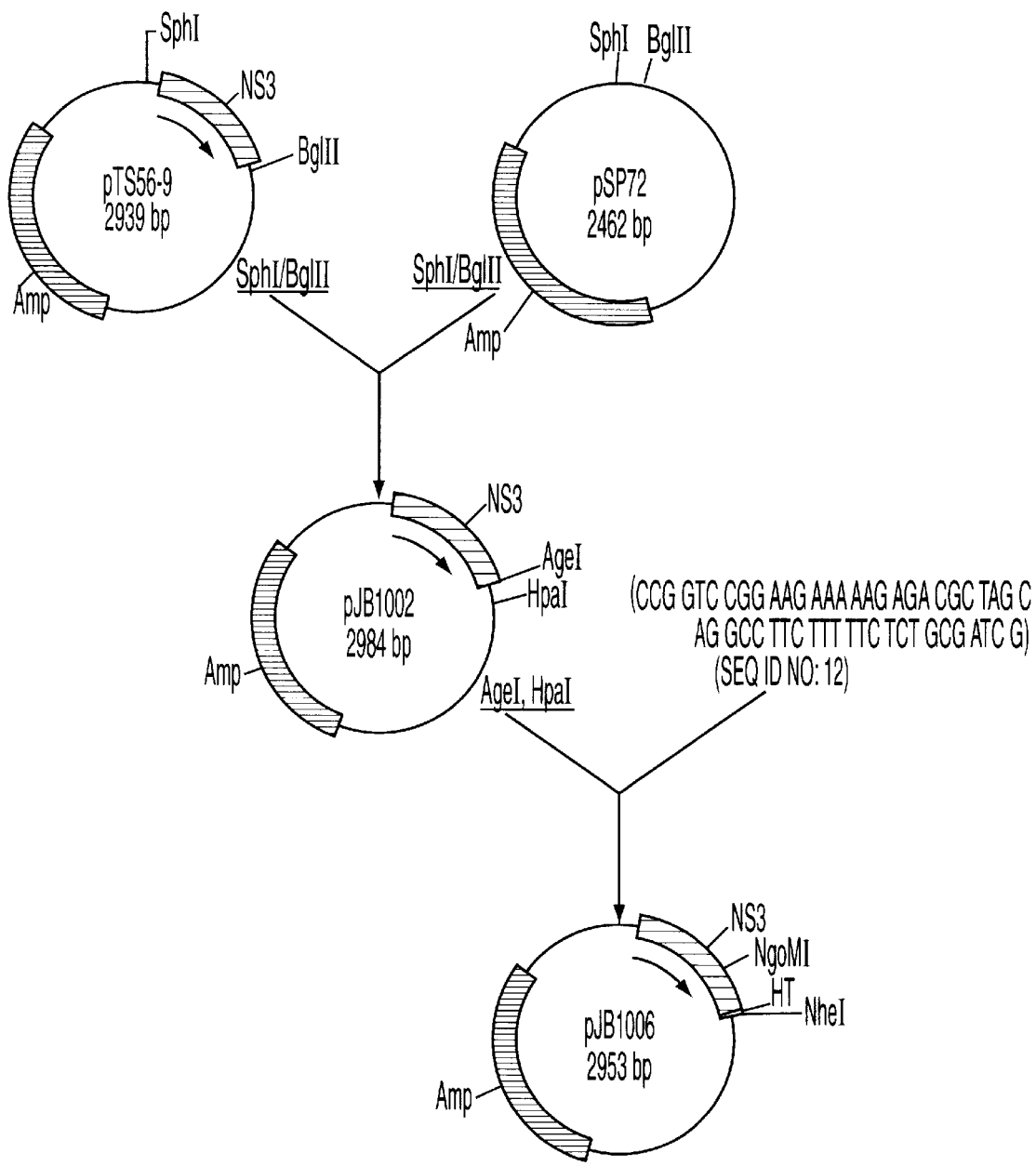
FIG. 4 depicts the recombinant synthesis of plasmid pJB1006.

(iii) Construction of the plasmid pJB 1006 Fused with a peptide of positively charged amino acids at the carboxy terminus of NS3 183 (FIG. 4).

The plasmid pTS 56-9 was digested with Sph I and Bgl II and the DNA fragment containing HCV sequence was isolated and cloned into a Sph I, Bgl II cut pSP72. The resulting plasmid pJB 1002 digested with Age I and HpaI and ligated to a double stranded oligonucleotide, (SEQ ID NO 12)
```
CCG GTC CGG AAG AAA AAG AGA CGC TAG C
    AG GCC TTC TTT TTC TCT GCG ATC G,
``` to construct pJB 1006. This fused the hydrophilic, solubilizing motif onto the NS3 protease.

Figure 5:
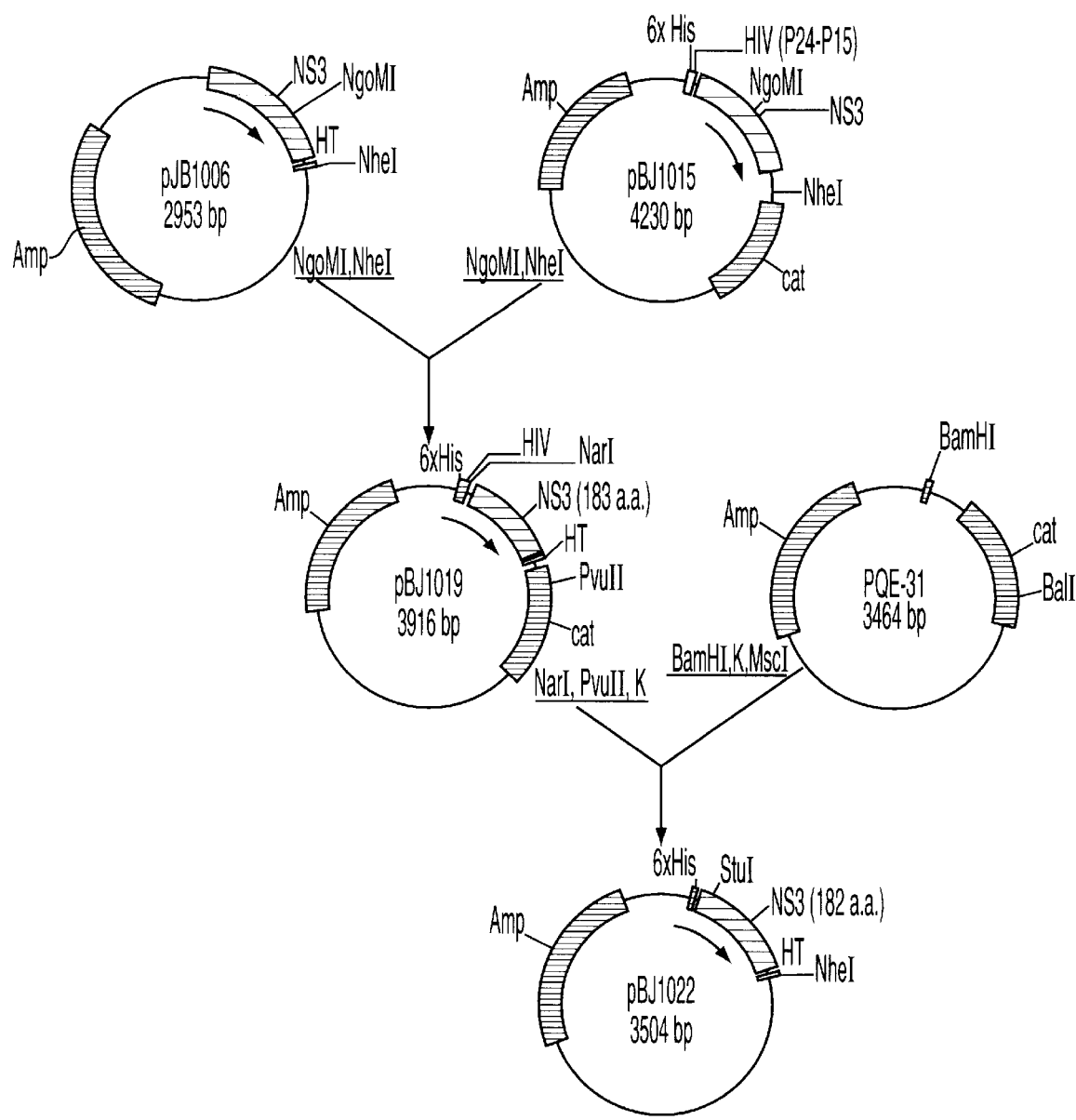
FIG. 5 depicts the recombinant synthesis of plasmid pBJ1022.

(iv) Construction of the Plasmid pBJ 1022 expressing His-NS3(183)-HT in *E.coli* (FIG. 5)

The plasmid pJB 1006 was digested with NgoM I and Nhe I and the 216 bp DNA fragment was isolated and cloned into Ngo M I, Nhe I cut pBJ 1015 to construct plasmid pBJ 1019. The plasmid pBJ 1019 was digested with Nar I and Pvu II, and treated with Klenow polymerase to fill in 5' ends of Nar I fragments. The expression plasmid pQE31 (Invitrogen) was digested with BamH I, blunt ended with Klenow polymerase. The 717 bp Nar I- Pvu II DNA fragment was isolated and ligated to the 2787 bp BamH I/Klenowed -Msc I (Bal I) fragment of the expression plasmid pQE31 (Invitrogen). The recombinant plasmid, pBJ 1022, obtained after transformation into *E.coli* expresses His NS3(2–183)-HT which does not contain any HIV protease cleavage site sequence. The plasmid also contains a large deletion in the CAT (Chloramphenicol Acetyl Transferase) gene.

Figure 6:
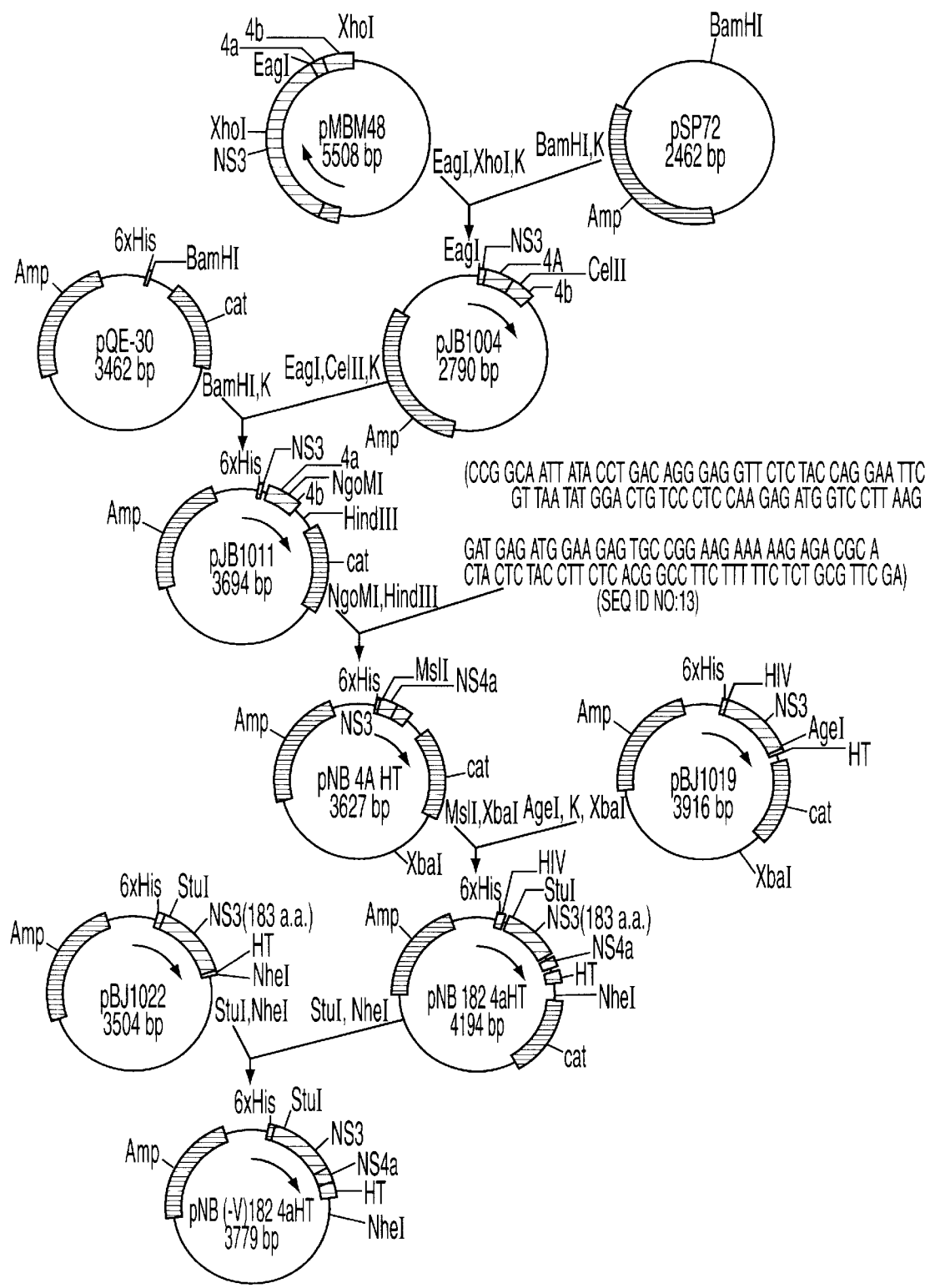
FIG. 6 depicts the recombinant synthesis of plasmid pNB(-V)182Δ4AHT.

(v) Construction of the Plasmid pNB(–V)182-Δ4A HT (FIG. 6)

The plasmid pMBM 48 was digested with Eag I and Xho I, treated with Klenow polymerase and the 320 bp DNA fragment was isolated and cloned into BamH I cut , blunt ended pSP 72 to construct the plasmid pJB1004. The 320 bp fragment encodes 7 amino acid from carboxy terminal of NS3(631), all of NS4A, and the amino terminal 46 amino acid of NS4B. The recombinant plasmid pJB1004 was digested with Eag I and Cel 2, blunt ended with KIenow polymerase. The 220 bp DNA fragment was isolated and cloned into the expression plasmid pQE30 which was digested with BamH I and blunt ended with Klenow polymerase prior to ligation. The resulting plasmid pJB 1011 was digested with NgoM I and Hind III and ligated to a double stranded oligonucleotide,

```
CCG GCA ATT ATA CCT GAC AGG GAG GTT CTC TAC CAG GAA TTC
    GT TAA TAT GGA CTG TCC CTC CAA GAG ATG GTC CTT AAG
```

Figure 7:
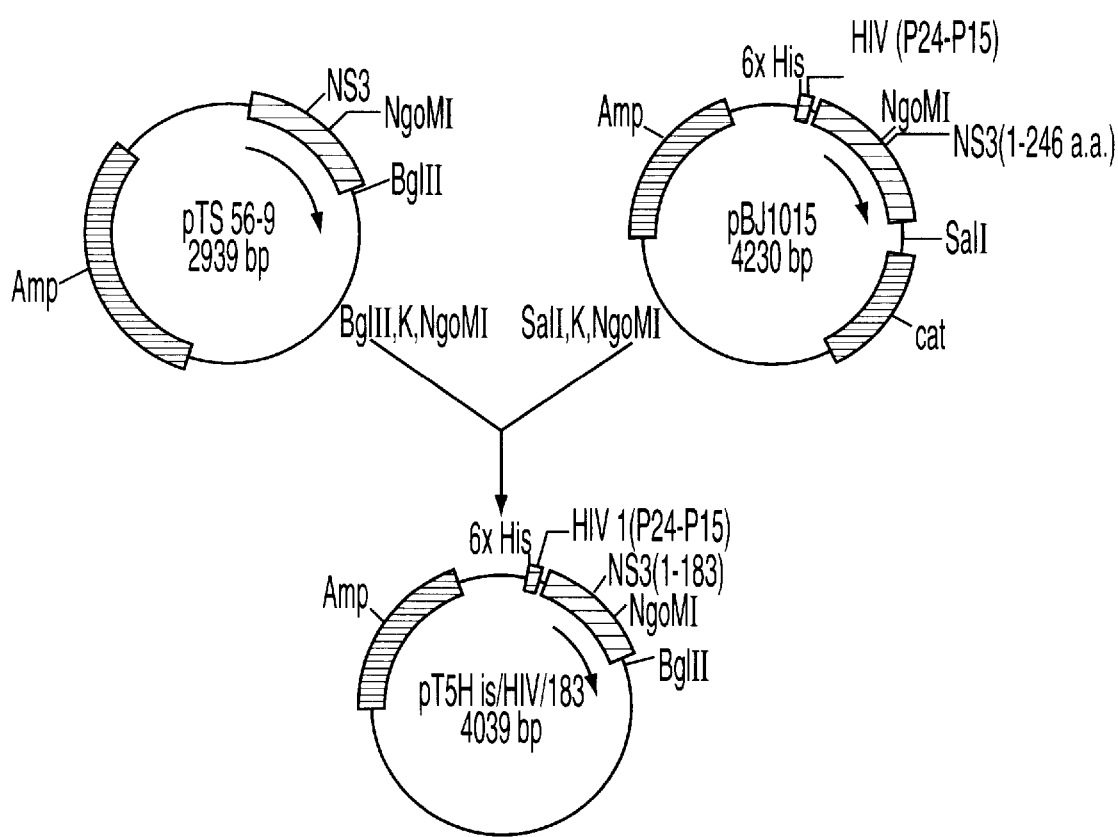
FIG. 7 depicts the recombinant synthesis of plasmid pT5His/HIV/183.

(SEQ ID NO 13)
```
GAT GAG ATG GAA GAG TGC CGG AAG AAA AAG AGA CGC A
CTA CTC TAC CTT CTC ACG GCC TTC TTT TTC TCT GCG TTC GA
``` to construct the plasmid pNB 4A HT. The plasmid pNB 4AHT was digested with MsI I and Xba I. The 1218 bp DNA fragment was isolated and cloned into Age I cut, klenow polymerase treated, Xba I cut vector DNA of pBJ 1019. The ligation results in a substitution of the 183rd amino acid residue valine by a glycine residue in NS3, and a deletion of amino terminal three amino acid residues of NS4A at the junction. The recombinant plasmid pNB182Δ4A HT comprising NS3(182aa)-G-NS4A(4–54 amino acid) does not contain NS3/NS4A cleavage site sequence at the junction and is not cleaved by the autocatalytic activity of NS3. Finally the plasmid pNB182Δ4A HT (SEQ ID NO 8) was digested with Stu I and Nhe I, the 803 bp DNA fragment was isolated and doned into Stu I and Nhe I cut plasmid pBJ 1022. The resulting plasmid pNB(−V)182-Δ4A HT contains a deletion of the HIV sequence from the amino terminus end of the NS3 sequence and in the CAT gene (SEQ ID NO 27).
(vi) Construction of the Plasmid pT5 His HIV-NS3 (FIG. 7)

The plasmid pTS56-9 was digested with Bgl II, and treated with Klenow polymerase to fill in 5' ends. The plasmid was then digested with NgoM I and the blunt ended Bgl II/NgoMI fragment containing the NS3 sequence was isolated and ligated to the Sal I, Klenow treated Ngo MI cut and Sal I klenowed pBJ 1015. The resulting plasmid is designated pT5His HIW 183.

EXAMPLE 2

Purification of HCV NS3 Protease having a Solubilizing Motif

Purification of His182HT (SEQ ID NO 4) and His (−V) 182Δ4AHT (SEQ ID NO 8

The recombinant plasmids pBJ1022 and pNB(−V) 182Δ4A were used to transform separate cultures of *E. coli* strain M15 [pREP4] (Qiagen), which over-expresses the lac repressor, according to methods recommended by the manufacturer. M15 [pREP4] bacteria harboring recombinant plasmids were grown overnight in broth containing 20g/L bactotrypton, 10g/L bacto-yeast extract, 5g/L NaCl and supplemented with 100 µg/ml ampicillin and 25 µg/ml kanamycin. Cultures were diluted down to O.D.600 of 0.1, then grown at 30° C. to O.D.600 of 0.6 to 0.8, after which IPTG was added to a final concentration of 1 mM. At post-induction 2 to 3 hours, the cells were harvested by pelleting, and the cell pellets were washed with 100 mM Tris, pH 7.5. Cell lysates were prepared as follows: to each ml equivalent of pelleted fermentation broth was added 50 µl sonication buffer (50 mM sodium phosphate, pH 7.8, 0.3M NaCl) with 1mg/ml lysozyme; cell suspension was placed on ice for 30 min. Suspension was then brought to a final concentration of 0.2% Tween-20, 10 mM dithiothreitol (DTT), and sonicated until cell breakage was complete. Insoluble material was pelleted at 12,000×g in a microcentrifuge for 15 minutes, the soluble portion was removed to a separate tube and the soluble lysate was then brought to a final concentration of 10% glycerol. Soluble lysates from cells expressing the plasmids produce strongly immunoreactive bands of the predicted molecular weight. Soluble lysates prepared for Ni$^{2+}$column purification were prepared with 10 mM β-mercaptoethanol (BME) instead of DTT. Lysates were stored at −80° C.

Purification using Ni$^{2+}$-Nitrosyl Acetic Acid (NTA) Agarose (OIAGEN)

The proteins were then purified by placing the extracted lysate on an NTA agarose column. NTA agarose column chromatography was used because the histidine tag which was fused to the N-terminus of the proteases readily binds to the nickel column. This produces a powerful affinity chromatographic technique for rapidly purifying the soluble protease. The column chromatography was performed in a batch mode. The Ni$^{2+}$ NTA resin (3ml) was washed twice with 50 ml of Buffer A (50mM sodium phosphate pH 7.8 containing 10% glycerol, 0.2% Tween-20, 10 mM BME). The lysate obtained from a 250 ml fermentation (12.5 ml) was incubated with the resin for one hour at 4° C. The flow through was collected by centrifugation. The resin was packed into a 1.0×4 cm column and washed with buffer A until the baseline was reached. The bound protein was then eluted with a 20 ml gradient of imidazole (0–0.5M) in buffer A. Eluted fractions were evaluated by SDS-PAGE and western blot analysis using a rabbit polyclonal antibody to His-HIV 183. The amount of soluble, active, HCV protease recovered was equal to about 5% of the total protein expressed by the cells as determined by the Bradford assay, U.S. Pat. No. 4,023,933.

Purification using POROS Metal-Chelate Affinity Column

In an alternative method to purify the proteins the lysate containing the proteins were applied to a POROS metal-chelate affinity column. Perfusion chromatography was performed on a POROS MC metal chelate column (4.6×50mm, 1.7 ml) precharged with Ni$^{2+}$. The sample was applied at 10 ml/min and the column was washed with buffer A. The column was step eluted with ten column volumes of buffer A containing 25 mM imidazole. The column was further eluted with a 25 column volume gradient of 25–250 mM imidazole in buffer A. All eluted fractions were evaluated by SDS-PAGE and western blot analysis using rabbit polyclonal antibody. The amount of soluble, active, HCV protease recovered was equal to about 5% of the total protein expressed by the cells as determined by the Bradford assay.

EXAMPLE 3

Peptide Synthesis of the 5A/5B and 4B1/5A Substrates

The peptides 5A/5B and 4B/5A substrates (SEQ ID NOs 16, 18,19,20 and 21) were synthesized using Fmoc chemistry on an ABI model 431A peptide synthesizer. The manufacture recommended FastMoc™ activation strategy (HBTU/HOBt) was used for the synthesis of 4A activator peptide. A more powerful activator, HATU with or without the additive HOAt were employed to assemble 5A/5B substrate peptides on a preloaded Wang resin. The peptides were cleaved off the resin and deprotected by standard TFA cleavage protocol. The peptides were purified on reverse phase HPLC and confirmed by mass spectrometric analysis.

EXAMPLE 4

HPLC-assay using a Synthetic 5A/5B Peptide Substrate

To test the proteolytic activity of the HCV NS3 protease the DTEDVVCC SMSYTWTGK (SEQ ID NO 16) and soluble HCV NS3 (SEQ ID NO 27) were placed together in an assay buffer. The assay buffer was 50 mM sodium phosphate pH 7.8, containing 15% glycerol, 10 mM DTT, 0.2% Tween20 and 200 mM NaCl). The protease activity of SEQ ID NO 27 cleaved the substrate into two byproduct peptides, namely 5A and 5B. The substrate and two byproduct peptides were separated on a reversed-phase HPLC column. (Dynamax, 4.6×250 mm) with a pore size of 300 Å and a particle size of 5 µm. The column was equilibrated with 0.1%TFA (Solvent A) at a flow rate of 1 ml per minute. The substrate and the product peptide standards were applied to the column equilibrated in A. Elution was performed with a acetonitrile gradient (Solvent B=100% acetonitrile in A). Two gradients were used for elution (5% to 70%B in 50 minutes followed by 70% to 100%B in 10 minutes).

In another experiment, partially purified SEQ ID NO 27 or vector control was incubated with 100 µM of substrate for 3, 7 and 24 hours at 30° C. The reaction mixture was quenched by the addition of TFA to 0.01% and applied to the reversed-phase HPLC column. The fractions from each run were evaluated by mass spectrometry and sequencing.

EXAMPLE 5

Analysis of NS3 Protease Activity By In Vitro Translation Assay

To detect HCV NS3 protease activity in trans, we have expressed a 40 kD protein containing the NS5A/5B cleavage site in cell-free translation system and used that as the substrate for the enzyme. The substrate protein produces two protein products of apparent molecular weight 12.5 kD (NS 5A') and 27 kD (NS5B') upon cleavage by the HCV NS3 protease.

The plasmid pTS102 encoding the substrate 5A/5B was linearized by digestion with EcoR I and was transcribed using T7 RNA polymerase in vitro. The RNA was translated in presence of $^{35}$S methionine in rabbit reticulocyte lysates according to the manufacturer's (Promega) protocol to produce HCV specific protein. In a 20 μl total reaction mixture containing 10 mM Tris, pH 7.5, 1 mM DTT, 0.5 mM EDTA, and 10% glycerol was placed 2 to 8 μl of $^{35}$S methionine-labeled translated 5A/5B substrate. The reaction was started with the addition of 10μl of HCV NS3 protease in solubilization buffer (50 mM Na Phosphate, pH 7.8, 0.3M NaCl, 0.2% Tween 20, 10 mM DTT or BME, 10% glycerol), and incubated at 30° C. for the specified time. Reactions were stopped by adding an equal volume of 2× Laemmli sample buffer (Enprotech Inc.) and heating at 100° C. for 3 minutes. Reaction products were separated by SDS PAGE electrophoresis; gels were fixed, dried and subjected to autoradiography.

The in vitro translated substrate was used to assay the HCV NS3 proteases expressed by E. coli harboring plasmids pBJ1022 and pNB(-V)182Δ4A (SEQ ID NOs 4 and 27). In a two hour assay incubated at 30° C., pBJ1022 crude soluble lysate at 3, 6, and 10μl, was able to cleave 5A/5B substrate in a dose responsive manner, producing the expected cleaved products: 5A (12.5 kD) and 5B (27 kD) as shown by SDS PAGE analysis. Corresponding vector control lysate did not show any cleavage activity over background. The crude soluble lysate derived from pNB182Δ4A was much more active in this assay. After only 30 minutes incubation, the 5A and 5B cleavage products were detected using as little as 0.125 μl cell lysate, with increasing amounts of lysate showing increased cleavage, reaching a maximum at 1 μl.

We performed a time course study of the NS3 Protease activity of pNB182Δ4A in an in vitro translation assay for further characterization of the activity. At 30° C., in a reaction containing the translated 5A/5B substrate plus pNB182Δ4A soluble lysate at 1 μl per 20 μl reaction volume, the 5A and 5B cleavage products appeared beginning at 1 minute, and increased with time at 2.5, 5, 10, and 20 minutes.

Since we were able to demonstrate HCV NS3 Protease activity using crude cell lysates of pBJ1022 and pNB182Δ4A, we wanted to at least partially purify the expressed proteins in an effort to remove bacterial proteases from these preparations. For this purpose, affinity column chromatography using $Ni^{2°}$ bound ligands was found to be effective, binding the histidine tag at the amino terminal ends of the expressed proteins, and subsequently releasing the bound proteins by imidazole elution. The imidazole-eluted fractions resulting from the purification of pNB182Δ4A on a Ni-NTA column were tested for activity in the in vitro translation assay. The resultant fractions were all able to cleave the translated 5A/5B Substrate, producing the expected 5A and 5B products. Background bacterial protease activity was not detected in these eluted fractions .

As was described above, pBJ1022 was purified by another method of $Ni^{2+}$ chelate chromatography, using POROS $Ni^{2+}$ chelate resin and perfusion chromatography. Imidazole-eluted fractions which were positive for immunoreactivity with antibody to NS3 183 were tested for HCV protease activity by in vitro translation assay. In order to optimize detection of activity in this assay for HCV protease, reactions were supplemented with a truncated peptide derived from the NS4A cofactor which has been shown to enhance cleavage at the 5A/5B site by NS3 protease . The cofactor was supplied as a synthetic peptide containing amino acids 22 to 54 of NS4A (strain HCV-BK) at a final concentration of 1 μM. All fractions tested were active in this translation assay.

EXAMPLE 6
ENHANCEMENT BY 4A PEPTIDES

NS4A is able to enhance the NS3 serine protease activity at NS5A/5B site in mammalian cells that transiently coexpress NS3, NS4A, and the various HCV non-structural polyprotein containing downstream cleavage sites . We have studied this enhancement activity in a well defined cell-free biochemical assay, using the partially purified E.coli-expressed pBJ1022 as a source of NS3 protease, and synthetic peptides containing various truncations of NS4A. In our first experiment we used a crude cell lysate of pBJ1022 as the enzyme and NS4A synthetic peptide truncated 33 mer from amino acid 22 to amino acid 54, the carboxy-terminal in vitro translation cleavage reaction . The C-terminal 33 amino add peptide of NS4A was able to enhance the activity of the NS3 catalytic domain in a dose dependent manner from 0.01 μM to 1.0 μM peptide, producing the expected products of 5A (12.5kD), and 5B (27kD) from the 40kD translated 5A/5B substrate. Without the 4A peptide a relatively low cleavage activity by the protease alone was observed at the short incubation time of 30 minutes. The 4A peptide itself or with the combination of crude lysate produced from cells harboring the vector plasmid did not cleave the substrate.

To further characterize NS4A enhancement activity additional truncations were made to the NS4A sequence. Truncated peptides were evaluated for their activity in the in vitro translation assay using $Ni^{2+}$ chelate column-purified pBJ1022 (NS3 catalytic domain). We observed that in addition to the C-terminal 33 amino acid peptide, a 18 amino acid peptide containing the NS4A sequence from amino acid 19 through 36 was able to enhance the NS3 mediated cleavage activity. Other peptides, including the N-terminal 21 amino acid, and two shorter truncations from the carboxyl terminal end, a 22 mer and a 15 mer, were found to have no effect; also a heterologous peptide of 18 amino add also had no enhancement activity.

DISCUSSION

The experiments described in this report dearly demonstrate that bacterially expressed HCV protease catalyzes cleavage of i) HCV polyproteins and ii) synthetic peptide substrates in trans biochemical assay. The processing activity of NS3 catalytic domain is enhanced by NS4A and its derivatives. The activity of the fusion protein containing the NS3 catalytic domain and NS4A is much superior to that of the NS3 catalytic domain alone.

Hydrophobicity analysis of the catalytic domain of the NS3 protease reveals that the protein is very hydrophobic and also it contains seven cysteine residues. To neutralize hydrophobicity and thus to improve solubility we have added six positively charged amino acid residues as a solubilizing motif. The addition of a solubilizing motif appears to improve the solubility without affecting the enzymatic activity.

We have also shown that the HCV NS4A from Japanese BK strain has enhanced the HCV-H NS3 mediated cleavage at 5A/5B site. This suggests that essential elements of recognition may be conserved among various strains of HCV.

It is clear from above experimental results that attachment of hydrophilic tail (solubilizing motif/water attracting structures) at the carboxy terminal end of histidine fused NS3 catalytic domain improved expression of soluble protein in E.coli. In these experiments six residues of positively charged amino acids are attached at the carboxy terminal end of the protein. Another example of a solubilizing motif is an amphipathic helix tail (peptides having charged and hydrophobic amino acid residues to form both charged and hydrophobic faces) which is fused to the HCV NS3 protease. Addition of an amphipathic helix at the carboxy terminus of such fusion proteins will be an alternative way to achieve improvement of solubility without affecting the enzymatic activity of the protease.

The hydrophilic tail used in these experiments consists of six amino acids. The sequence and length of the hydrophilic amino adds can be varied to achieve optimal expression of soluble protein. Therefore size of the solubilizing motif and nature of charged residues may effect the expression of soluble NS3 in E.coli.

Position of these water attracting structures/motifs at both ends, at one end (amino terminal or carboxy terminal), or insertion within the NS3 catalytic domain and NS3 (catalytic domain)-4A fusion protein, may improve solubility of the protein without affecting the activity.

Based on sequence homology to the members of trypsin superfamily and the protease of other members of the flaviviruses, it is predicted that the amino terminal 181 amino add of NS3 is the catalytic domain of HCV NS3 protease. Recently it has also been shown that a protein of 169 amino add containing a 10 amino acid deletion from the amino terminus and 2 amino acid from carboxy terminal of the catalytic domain retains full enzymatic activity. The model we have developed predicts that a protein of 154 amino acids containing a deletion of 26 amino acid from amino terminal and a deletion of 2 amino acid from the carboxyl terminus would retain full enzymatic activity for the 5A/5B substrate.

Analysis of the amino acid sequence of the catalytic domain of NS3 protease reveals that the protein contains seven cysteine residues, an odd number, which may cause aggregation. Mutation of one cysteine residue (located on the surface of the protein molecule and not involved in the activity) may improve solubility of the protein without affecting the protease activity.

Using the cell free biochemical assay we have demonstrated that the synthetic peptide containing 18 amino add of HCV NS4A protein is sufficient to enhance the cleavage at NS5A/5B site mediated by the catalytic domain of NS3.

EXAMPLE 7

Refolding of Insoluble HCV NS3 Protease

The present example describes a novel process for the refolding of HCV NS3 protease which does not have a solubilizing motif from an E.coli inclusion body pellet. This procedure can be used to generate purified enzyme for activity assays and structural studies.

Extraction and Purification of His-HIV 183 from the E.coli inclusion Body Pellet E. coli cells harboring the plasmid for HisHIV183 was used to transform a culture of E. coli strain M15 [pREP4] (Qiagen), which over-expresses the lac repressor, according to methods recommended by commercial source. M15 [pREP4] bacteria harboring recombinant plasmids were grown overnight in 20-10-5 broth supplemented with 100µg/ml ampicillin and 25 µg/ml kanamycin. Cultures were diluted to O.D.600 of 0.1, then grown at 37° C. to O.D.600 of 0.6 to 0.8, after which IPTG was added to a final concentration of 1 mM. At post-induction 2 to 3 hours, the cells were harvested by pelleting, and the cell pellets were washed with 100 mM Tris, pH 7.5. were pelleted by centrifugation. The cell pellet was resuspended in 10 ml of 0.1M Tris-HCl, 5mM EDTA, pH 8.0 (Buffer A) for each gm wet weight of pellet. The pellet was homogenized and resuspended using a Dounce homogenizer. The suspension was clarified by centrifugation at 20,000×g for 30 minutes at 4° C. The pellet was sequentially washed with the following five buffers:

1. Buffer A
2. 10M sodium chloride (NaCi) in buffer A
3. 1.0% Triton X-100 in buffer A
4. Buffer A
5. 1.0M Guanidine HCl (GuHCl) in buffer A.

The washed pellet was solubilized with 5M GuHCl, 1% beta mercaptoethanol in buffer A (3 ml per gm wet wt. of pellet) using a Dounce homogenizer and centrifuged at 100,000×g for 30 minutes at 4° C. Purification of denatured HisHIV183 from high molecular weight aggregates was accomplished by size exclusion on a SEPHACRYL S-300 gel filtration column.

In particular, an 8 ml sample of the 5.0M GuHCl E. coli extract was applied to a 160 ml Pharmacia S300 column (1.6×100 cm) at a flow rate of 1.0 ml/min. The column buffer was comprised of 5.0M GuHCl, 0.1M Tris-HCl, pH 8.0, and 5.0 mM EDTA. The fraction size was 5.0 ml. Appropriate fractions were pooled based on the results of SDS-PAGE, as well as N-terminal sequence analysis of the protein transferred to a Pro-Blot.

Detergent-Assisted refolding of HCV-protease

The protein was concentrated by ultrafiltration using a 43 mm Amicon YM10 membrane to 1.0 mg per ml in 5M GuHCl, 0.1M Tris-HCl pH 8.0, 1.0 mM EDTA, 1.0% beta-mercaptoethanol. It was then diluted 50-fold to 0.1M GuHCl in refolding buffer (100 mM sodium phosphate pH 8.0, 10 mM DTT, 0.1% lauryl maltoside) and the mixture was incubated on ice for at least one hour. A 25 ml sample containing 500 µg of the protein in the refolding buffer was applied to a Pro-RPC HR ⅗ reversed phase chromatography column. The applied sample contained 500 µg protein in 25 ml of refolding buffer. To the column was then applied a solution B comprised of 99.9% $H_2O$+0.1% trifluoroacetic acid (TFA). A 10 ml volume of solution C [10% $H_2O$, 90% acetonitrile (AcN)+0.1% TFA] was applied to the column at a 0–60% gradient into solution B at a flow rate of 0.5ml/min. and a fraction size of 0.5 ml. The fractions were monitored at A214; 2.0 absorbance units full scale (AUFS).

Fractions containing the protein (corresponding to peak 1) were pooled for renaturation by stepwise dialysis. The fractions were first dialysed in 0.1% TFA in 25% glycerol overnight at 4° C.; then dialyzed in 0.01% TFA in 25% glycerol overnight at 4° C.; then dialyzed in 0.001% TFA in 25% glycerol for 3.0 hours; then dialyzed for 3 hours at 4° C. in 50 mM $NaPO_4$, pH 6.0, 10 mM dithioreitol (DTT) in 25% glycerol. The protein was then dialyzed for 3.0 hours at 4° C. in 50 mM NaPO4, pH 7.0, 0.15 M NaCl, 10 mM DTT in 25% glycerol; and then finally dialyzed in 50 mM NaPO4, pH 7.8, 0.3 M NaCl, 10 mM DTT, 0.2% Tween 20 in 25% glycerol. This resulted in purified, refolded, soluble, active HCV NS3 protease.

Far UV circular dichroism (CD) analysis of the protein was used to monitor the refolding from an acid denatured state to a folded state at neutral pH. The protein recovery was monitored by a UV scan and SDS-PAGE analysis.

RESULTS

Detergent-Assisted Refolding of His-HIV183

HisHIV183 was quantitatively extracted from an E. coli inclusion body pellet. SDS-PAGE analysis at the various stages of extraction shows that sequential washes are essential to remove significant amounts of the contaminating proteins. HisHIV183 was extracted from the washed inclusion body pellet in the presence of 5M GuHCI. The 5M GuHCl extract was applied to a SEPHACRYL S-300 column and the appropriate fractions were pooled based on SDS-PAGE analysis. The amino acid sequence of the first ten residues was verified.

Refolding was performed at very low concentrations of protein, in the presence of DTT, lauryl maltoside and glycerol at 4° C. The diluted protein was concentrated on a Pro-RPC reversed phase column. Two peaks were obtained based on the UV and protein profile. Only Peak 1 has yielded soluble protein after stepwise dialysis. Far UV CD spectral analysis was used to monitor refolding from a denatured state at acid pH to a folded state at neutral pH. At pH 7.4, the protein was found to exhibit significant amounts of secondary structure that is consistent with that of beta sheet protein. At low pH, the CD spectrum showed that it is fully random coil, having a minimal molar ellipticity at 200 nm. The ratio of this minimum at 200 nm to that of the shoulder at 220 nm is approximately 4:1. This ratio decreased when the secondary structure formation occurred at neutral pH.

A UV scan at each step of dialysis showed that the protein recovery was >90% up to pH 7.4 and that there was no light scattering effect due to protein aggregates. SDS-PAGE analysis also indicated that there was no loss of protein up to pH 7.0 during refolding. Precipitation of protein occurred at the last step of dialysis, and the soluble protein was clarified by centrifugation. The overall protein recovery was about 0.10%. The refolded protein was found to be active in a trans-deavage assay using the in vitro-translated 5A/5B substrate in the presence of 4A peptide.

EXAMPLE 8

Analysis of Refolded NS3 Protease Activity by In Vitro Translation Assay

To detect HCV NS3 protease activity in trans, we have expressed a 40 kD protein containing the NS5A/5B cleavage site in cell-free translation system and used that as the substrate for the enzyme. The substrate protein produces two protein products of apparent molecular weight 12.5 kD (NS 5A') and 27 kD (NS5B') upon cleavage by the HCV NS3 protease.

The plasmid pTS102 encoding the substrate 5A/5B was linearized by digestion with EcoR I and was transcribed using T7 RNA polymerase in vitro. The RNA was translated in presence of $^{35}$S methionine in rabbit reticulocyte lysates according to the manufacturer's (Promega) protocol to produce HCV specific protein. In a 20 µl total reaction mixture containing 10 mM Tris, pH 7.5, 1 mM DTT, 0.5 mM EDTA, and 10% glycerol was placed 2 to 8 µl of $^{35}$S methionine-labeled translated 5A/5B substrate. The reaction was started with the addition of 10 µl of HCV NS3 protease (SEQ ID NO: 5) with an approximately equimolar amount (2 µM) of the carboxyterminal 33 mer cofactor NS4A (SEQ ID NO: 29) in solubilization buffer (50mM Na Phosphate, pH 7.8, 0.3M NaCl, 0.2% Tween 20, 10 mM DTT or BME, 10% glycerol), and incubated at 30° C. for about one hour. Reactions were stopped by adding an equal volume of 2× Laemmli sample buffer (Enprotech Inc.) and heating at 100° C. for 3 minutes. Reaction products were separated by SDS PAGE electrophoresis; gels were fixed, dried and subjected to autoradiography.

The assay was able to cleave 5A/5B substrate in a dose responsive manner, producing the expected cleaved products: 5A (12.5 kD) and 5B (27 kD) as shown by SDS PAGE analysis. The production of cleaved 5A and 5B polypeptides from the 5A/5B substrate is proof that soluble, active, refolded HCV protease was indeed produced by the process of example 7.

EXAMPLE 9

Surface Plasmon Resonance Assay

Figure 8A:
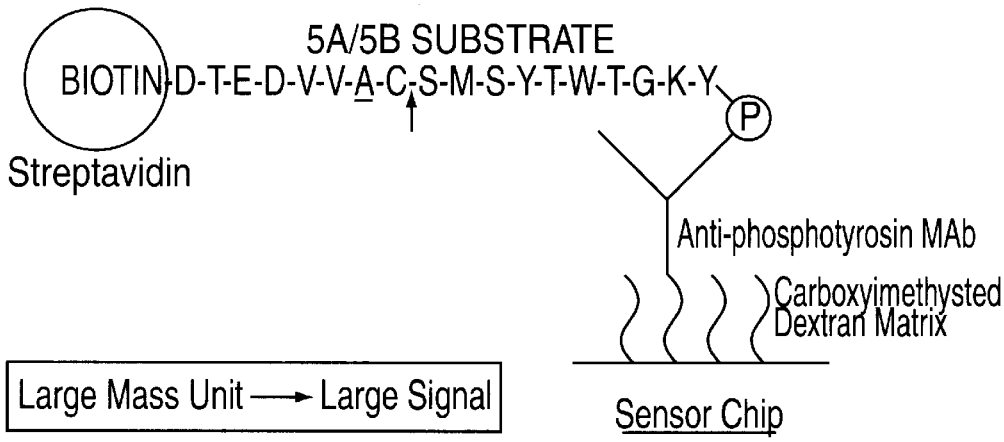
FIG. 8A and 8B schematically depicts a high throughput assay for discovering HCV protease inhibitors using surface plasmon resonance technology.
Figure 8B:
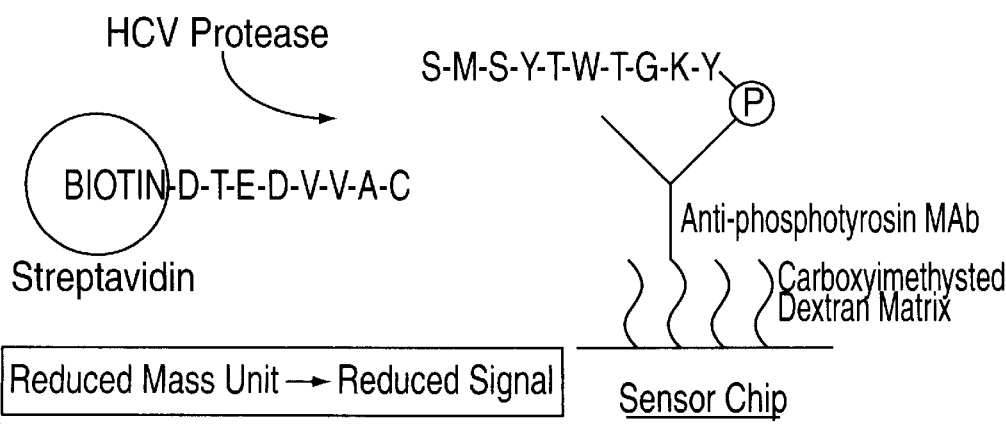

The present example illustrates a method for determining if a compound can be useful as an HCV protease inhibitor using the surface plasmon resonance assay. FIGS. 8A and 8B illustrate the technique.

BIAcore™ is a processing unit for Biospecific Interaction Analysis. The processing unit integrates an optical detection system with an autosampler and a microfluidic system. BIAcore™ uses the optical phenomena, surface plasmon resonance to monitor interaction between biomolecules. SPR is a resonance phenomenon between incoming photons and electrons on the surface of thin metal film. Resonance occurs at a sharply defined angle of incident light. At this angle, called the resonance angle, energy is transferred to the electrons in the metal film, resulting in a decreased intensity of the reflected light. SPR response depends on a change in refractive index in the dose vicinity of the sensor chip surface, and is proportional to the mass of analyte bound to the surface. BIAcore continuously measure the resonance angle by a relative scale of resonance units (RU) and displays it as an SPR signal in a sensorgram, where RU are plotted as a function of time.

In addition, BIAcore™ uses continuous flow technology. One interactant is immobilized irreversibly on the sensor chip, comprising a non-crosslinked carboxymethylated dextran providing a hydrophilic environment for bimolecular interaction. Solution containing the other interactant flow continuously over the sensor chip surface. As molecules from the solution bind to the immobilized ligand, the resonance angle changes resulting in a signal registered by the instrument.

In this methodology, the enzymatic reactions are carried out outside of the BIAcore, i.e. in reaction tubes or 96-well tissue culture plates, as it is conventionally done for any of the currently available high throughput assays. The SPR is only used as a detection means for determination of the amount of an intact substrate remaining in a solution with and without the enzyme after the reaction is quenched.

In order to measure the amount of the intact substrate prior to the addition of enzyme, a means of capturing the substrate onto the sensor chip had to be established. In addition, to satisfy the requirement for a high throughput assay on the BIAcore, the substrate needed to be removed from the surface subsequent to completion of analysis. This is required since the same surface will be used for the subsequent reactions. To accomplish these two requirements, a phosphotyrosine is synthetically attached to one end of the substrate. The phosphotyrosine was chosen due to the commercial availability of an anti-phosphotyrosine monoclonal antibody. The antibody is covalently attached to the sensor chip by standard amine coupling chemistry. The anti-phosphotyrosine antibody, bound permanently to the chip is used to capture the phosphotyrosine-containing substrate in a reversible manner. The antibody-phosphotyrosine interaction is ultimately used to capture and release the peptide substrate when desired by regeneration of the surface with various reagents i.e. 2M MgCl$_2$.

Introduction of the intact peptide onto the antibody surface results in a larger mass which is detected by the instrument To follow the extent of peptide cleavage, a mixture of peptide substrate and enzyme is incubated for the desired time and then quenched. Introduction of this mixture containing the cleaved peptide and the intact peptide to a regenerated antibody surface results in a lower mass value than that detected for a sample containing only intact peptide. The difference in the two values is then used to calculate the exact amount of intact peptide remaining after cleavage by the enzyme.

Although the reduction in mass can be directly followed with many large substrates, due to the small mass of a typical synthetic peptide substrate (10–20 amino acids, 1–3 Daltons), the mass difference, and thus the signal difference between the intact and cleaved peptide is very small within the signal to noise ratio of the instrument. To circumvent this low sensitivity, we attached a biotin at the N-terminus of the peptide. By addition and thus tagging of peptide with streptavidin prior to injection of tagged peptide onto the antibody surface of the chip, the signal due to the presence of streptavidin will be higher. Using this approach, a cleaved peptide lacking the N-terminal half, tagged with streptavidin will result in a much lower signal.

The HCV protease 5A–5B peptide substrate, DTEDVVACSMSYTWTGK (SEQ ID NO 18) was synthesized with an additional phosphotyrosine at the C-terminus and biotin at the N-terminus. The biotin was then tagged with streptavidin. An anti-phosphotyrosine monoclonal antibody, 4G10 (Upstate Biotechnology Inc., Lake Placid, N.Y.) was coupled to the sensor chip. In the absence of HCV protease, the intact, streptavidin-tagged biotinylated phosphotyrosine peptide results in a large signal (large mass unit/large signal) through its interaction with the anti-phosphotyrosine monoclonal antibody (Mab).

The protease-catalyzed hydrolysis of the phosphotyrosine-biotinylated peptide was carried out in a 96 well plate. The reaction was stopped with an equal volume of mercuribenzoate. The cleaved peptide which lacks the tagged streptavidin (less mass) results in the loss of response units (lower signal).

Using this method, numerous compounds can be tested for their inhibitory activity since the antibody surface can be regenerated repetitively with 2M MgCl$_2$.

Procedure for Coupling Anti-phosphotyrosine Mab to the Sensor Chip

The anti-phosphotyrosine Mab is coupled to the carboxymethylated dextran surface of a sensor chip in the following manner. The flow rate used throughout the coupling procedure is 5 $\mu$l/min. The surface is first activated with a 35 $\mu$l injection of NHS/EDC (N-hydroxysuccinimide/N-dimethyllaminopropyl-N'-ethylcarbodiimide-HCl). This is followed by a 40 ml injection of Mab 4G10 at 50 $\mu$g/ml in 10 mM sodium acetate buffer, pH=4.0. Any remaining activated esters are then blocked by the injection of 35 $\mu$l of 1M ethanolamine. These conditions result in the immobilization of approximately 7,500 response units (420 $\mu$M) of antibody.

Binding of Peptide and Regeneration of Mab 4G10 Surface

The flow rate used throughout the BIAcore analysis run is 5 $\mu$l/min. A 4 $\mu$l injection containing streptavidin-tagged peptide (peptide concentration at 2 $\mu$M, streptavidin binding sites concentration at 9 $\mu$M) is carried out. The amount of streptavidin-tagged peptide bound to the antibody surface (in response units) is measured 30 seconds after the injection is complete.

Regeneration of Sensor Chip Surface

Regeneration of the Mab 4G10 surface is achieved using a 4 $\mu$l pulse of 2M MgCl$_2$ after each peptide injection. Surfaces regenerated up to 500 times still showed 100% binding of tagged peptide.

Determination of the Optimal Concentration of Peptide and Streptavidin

To determine the optimal peptide concentration, a standard curve was generated using various amounts of peptide (0–10 $\mu$M) in the presence of excess streptavidin. A value in the linear range, 2 $\mu$M, was chosen for standard assay conditions.

The amount of streptavidin required to completely tag the peptide was determined using a peptide concentration of 2.5 $\mu$M and titrating the amount of streptavidin ($\mu$M of binding sites). All the peptides were shown to be completely tagged when streptavidin concentrations greater than 3 $\mu$M (approximately equimolar to the peptide concentration) were used. A streptavidin concentration of 9 $\mu$M (a 4.5 fold excess) was chosen for standard assay conditions.

Application of Described Methodology to HCV Protease

The HCV protease 5A/5B peptide substrate, DTEDVVACSMSYTWTGK (SEQ ID NO 18), with phophotyrosine at the C-terminal and biotin at the N-terminal is synthesized. Anti-phosphotyrosine monoclonal antibody, 4G10 was coupled to the sensor chip.

In the absence of HCV protease, the intact streptavidin-tagged biotinylated phosphotyrosine peptide results in a large signal (large mass unit/large response units) through its interaction with the anti-phosphotyrosine monoclonal antibody.

The protease-catalyzed hydrolysis of the phosphotyrosine-biotinylated peptide was carried out in a 96 well plate. The reaction was stopped with an equal volume of the quenching buffer containing mercuribenzoate. Streptavidin was added to tag the peptide which binds to the biotin. The cleaved peptide which lacks the tagged streptavidin (less mass) results in the loss of response units.

Using this assay, numerous compounds can be tested for their inhibitory activity since the antibody surface can be regenerated repetitively with 2M MgCl$_2$.

The peptide cleavage activity by HCV protease can be monitored in a time dependent manner using the BIAcore-based methodology. Using the concentrated enzyme and the BIAcore substrate, Biotin-DTEDVVAC SMSYTWTGK-pY (SEQ ID NO 17), 50% substrate cleavage is achieved within 1 hour using the BIAcore-based HCV assay. Based on the amount of enzyme, His-NS3(183)$\Delta$4AHT needed to reach a 50% cleavage within 2 hours, a time scale desired for a development of a high throughput assay, we estimate that 1 liter of fermentation of the His-NS3(183)$\Delta$4AHT construct results in enough protease to run at least 100 reactions on the BIAcore.

Standard Operating Procedure for BIAcore-based HCV Assay

Reactions are prepared in a 96-well tissue culture plate using the Reaction Buffer (50 mM HEPES, pH 7.4, 20 % glycerol, 150 mM NaCl, 1 mM EDTA, 0.1% Tween-20,1 mM DIT) as diluent. The final reaction volume is 100 $\mu$l. Sample with the peptide alone (Biofin-DTEDVVAC SMSYTWTGKpY) is prepared by addition of 10 $\mu$l of peptide stock at 100 $\mu$M (prepared in the reaction buffer) to 90 $\mu$l of reaction buffer, so that the final concentration of peptide is 10 $\mu$M. Samples comprised of peptide and the enzyme are prepared by addition of 10 μl of peptide stock at 100 μM and 10 μl of partially purified His-NS3 (183)-Δ4A-HT stock at 1.7 mg/ml (both prepared in the reaction buffer) to 80 μl of reaction buffer, so that the final concentration of peptide and the enzyme is 10 and 0.1 μM respectively. The reaction is held at 30° C. for the specified time and then quenched. Quenching is achieved by transferring a 20-μl aliquot of the reaction mixture to a new tissue culture plate containing an equal volume of PMB Quenching Buffer (50 mM HEPES, pH 7.8, 150 mM NaCl, 5 mM P-Hydroxymercuribenzoic Acid, and 13 mM EDTA).

To prepare the quenched reaction mixture for injection onto the sensor surface, 30 μl PMB BIAcore Buffer (50 mM HEPES, pH 7.4, 1M NaCi) and 30 μl of streptavidin at 0.5 mg/ml in water is added to the 40 μl of the quenched reaction mixture to a final volume of 100 μl. In this step, all the peptides are tagged with streptavidin prior to the injection of samples. Finally, 4 μl of this sample is injected over the antiphosphotyrosin surface for determination of the intact versus cleaved peptide. The final concentration of peptide and the streptavidin in the BIAcore sample is 2 and 9 μM respectively.

| Experimental Conditions: | |
|---|---|
| Substrate: | Biotin-DTEDVVAC SMSYTWTGK-pY (SEQ ID NO 19) in Reaction buffer without DTT |
| Concentration: | 170 μM (Crude peptide, based on weight) |
| Enzyme: | 10 μl of concentrated His-NS3 (183)-Δ4A-HT at 1.7 mg/ml |
| Reaction volume: | 100 μl |
| Reaction buffer: | 50 mM HEPES, pH 7.8 |
|  | 20% glycerol |
|  | 150 mM NaCl |
|  | 1 mM EDTA |
|  | 1 mM DTT |
|  | 0.1% Tween-20 |
| Temp: | 30° C. |
| Quench with: | ρ-hydroxymercuribenzoate |

We claim:

1. An isolated soluble, active covalent HCV NS3–NS4A complex which consists of the catalytic domain of native HCV NS3 protease fused to an HCV NS4A cofactor, wherein said cofactor has been modified by deletion or substitution of one or more amino acid residues to prevent cleavage by the HCV NS3 protease.

2. The covalent HCV NS3–NS4A complex of claim further comprising a solubilizing motif fused to said complex.

3. The covalent HCV NS3–NS4A complex of claim 2 wherein the solubilizing motif is a polypeptide comprising Lys or Arg amino acid residues.

4. The covalent HCV NS3–NS4A complex of claim 2 wherein the solubilizing motif is defined by SEQ ID NO: 2, SEQ ID NO: 23 or SEQ ID NO: 24.

5. The covalent HCV NS3–NS4A complex of claim 1 or 2 having a sequence defined by SEQ ID NO: 7, SEQ ID NO: 8, SEQ ID NO: 9, SEQ ID NO: 10 or SEQ ID NO: 27.

* * * * *